US 8,235,979 B2

(12) United States Patent
Morgan et al.

(10) Patent No.: US 8,235,979 B2
(45) Date of Patent: *Aug. 7, 2012

(54) INTERFACING MEDIA MANIPULATION WITH NON-ABLATION RADIOFREQUENCY ENERGY SYSTEM AND METHOD

(75) Inventors: Roy E. Morgan, Alameda, CA (US); Wayne K. Auge, II, Sante Fe, NM (US)

(73) Assignee: NuOrtho Surgical, Inc., Fall River, MA (US)

(*) Notice: Subject to any disclaimer, the term of this patent is extended or adjusted under 35 U.S.C. 154(b) by 69 days.

This patent is subject to a terminal disclaimer.

(21) Appl. No.: 12/757,021

(22) Filed: Apr. 8, 2010

(65) Prior Publication Data

US 2010/0262136 A1    Oct. 14, 2010

Related U.S. Application Data

(60) Continuation-in-part of application No. 12/580,195, filed on Oct. 15, 2009, which is a continuation-in-part (Continued)

(30) Foreign Application Priority Data

Jun. 6, 2003    (WO) .................... PCT/US03/018116

(51) Int. Cl.
*A61B 18/14*    (2006.01)
(52) U.S. Cl. ................. 606/32; 606/41; 606/45; 606/49
(58) Field of Classification Search .................... 606/32, 606/41
See application file for complete search history.

(56) References Cited

U.S. PATENT DOCUMENTS 3,911,107 A    10/1975    Krezanoski
(Continued)

FOREIGN PATENT DOCUMENTS

GB    2037920    7/1980
(Continued)

OTHER PUBLICATIONS

Babincova, Melina, et al., "High-Gradient Magnetic Capture of Ferrofluids: Implications for Drug Targeting and Tumor Embolization", *Zeitschrift fur Naturforschung*, vol. 56-C, 2001, pp. 909-911.

(Continued)

*Primary Examiner* — Lee S Cohen
(74) *Attorney, Agent, or Firm* — Janeen Vilven; Peacock Myers, P.C.

(57) ABSTRACT

The effects produced by surgical devices that deploy an electrical circuit between electrodes are dependent on the nature of electrical work perform upon the conductive media in an around biologic tissues. Non-ablation radiofrequency surgical devices utilize a protective housing that provides, based upon procedure-specific needs, the ability to 1. move, manipulate, and segregate near-field effects both tangentially and perpendicularly to the tissue surface, 2. deliver far-field electromagnetic effects to tissue unencumbered by current deposition, and 3. serve as a 20 mechanical adjunct to and a selective throttling vent/plenum for energy delivery. Because the electrodes are non-tissue-contacting, this study characterizes the effects that non-ablation radiofrequency energy exerts upon interfacing media typically encountered during surgical applications. These devices create a Repetitive Molecular Energy Conversion Loop for surgical work; and, non-ionizing electromagnetic forces are deployed in strength levels that can produce thermal and non-thermal biologic tissue effects. A differential between current density dispersion and electromagnetic field strength is exploited to allow normal tissue healing responses to the near-field effects of tissue modification and preconditioning while permitting far-field effects, which are useful for inducing therapeutic biologic responses, to manifest in treated tissues that have been protected from electrical current generated collateral damage.

11 Claims, 15 Drawing Sheets

Related U.S. Application Data of application No. 12/479,578, filed on Jun. 5, 2009, now Pat. No. 7,819,864, which is a division of application No. 11/847,216, filed on Aug. 29, 2007, now Pat. No. 7,549,989, which is a division of application No. 11/147,481, filed on Jun. 7, 2005, now Pat. No. 7,354,438, which is a division of application No. 10/119,671, filed on Apr. 9, 2002, now Pat. No. 6,902,564, application No. 12/757,021, which is a continuation-in-part of application No. 12/486,616, filed on Jun. 17, 2009, and a continuation-in-part of application No. 11/006,079, filed on Dec. 6, 2004, now Pat. No. 7,771,422, which is a continuation-in-part of application No. PCT/US03/18116, filed on Jun. 6, 2003.

(60) Provisional application No. 60/312,965, filed on Aug. 15, 2001, provisional application No. 60/387,775, filed on Jun. 10, 2002, provisional application No. 60/387,114, filed on Jun. 6, 2002.

(56) References Cited

U.S. PATENT DOCUMENTS

| | | |
|---|---|---|
| 3,941,135 A | 3/1976 | von Sturm et al. |
| 3,982,017 A | 9/1976 | Thiele |
| 4,014,777 A | 3/1977 | Brown |
| 4,105,017 A | 8/1978 | Ryaby et al. |
| 4,266,532 A | 5/1981 | Ryaby et al. |
| 4,266,533 A | 5/1981 | Ryaby et al. |
| 4,504,493 A | 3/1985 | Marshall et al. |
| 4,540,409 A | 9/1985 | Nystrom et al. |
| 4,615,347 A | 10/1986 | Schooley |
| 4,872,865 A | 10/1989 | Bloebaum et al. |
| 4,938,970 A | 7/1990 | Hustead et al. |
| 4,971,068 A | 11/1990 | Sahi |
| 5,014,699 A | 5/1991 | Pollack et al. |
| 5,236,456 A | 8/1993 | O'Leary et al. |
| 5,282,861 A | 2/1994 | Kaplan |
| 5,304,724 A | 4/1994 | Newton |
| 5,314,476 A | 5/1994 | Prewett et al. |
| 5,352,463 A | 10/1994 | Badylak et al. |
| 5,360,440 A | 11/1994 | Andersen |
| 5,366,443 A | 11/1994 | Eggers et al. |
| 5,403,825 A | 4/1995 | Lagarde et al. |
| 5,458,596 A | 10/1995 | Lax et al. |
| 5,494,538 A | 2/1996 | Kirillov et al. |
| 5,498,259 A | 3/1996 | Mourant et al. |
| 5,514,130 A | 5/1996 | Baker |
| 5,516,533 A | 5/1996 | Badylak et al. |
| 5,554,141 A | 9/1996 | Wendler |
| 5,569,242 A | 10/1996 | Lax et al. |
| 5,584,863 A | 12/1996 | Rauch et al. |
| 5,622,725 A | 4/1997 | Kross |
| 5,669,904 A | 9/1997 | Platt et al. |
| 5,669,907 A | 9/1997 | Platt et al. |
| 5,669,934 A | 9/1997 | Sawyer |
| 5,683,366 A | 11/1997 | Eggers et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,741,261 A | 4/1998 | Moskovitz et al. |
| 5,746,896 A | 5/1998 | Shimamune et al. |
| 5,749,895 A | 5/1998 | Sawyer et al. |
| 5,788,976 A | 8/1998 | Bradford |
| 5,800,385 A | 9/1998 | Demopulos et al. |
| 5,820,583 A | 10/1998 | Demopulos et al. |
| 5,824,015 A | 10/1998 | Sawyer |
| 5,840,166 A | 11/1998 | Kaneko |
| 5,855,608 A | 1/1999 | Brekke |
| 5,860,950 A | 1/1999 | Demopulos et al. |
| 5,871,469 A | 2/1999 | Eggers et al. |
| 5,885,277 A | 3/1999 | Korth |
| 5,885,292 A | 3/1999 | Moskovitz et al. |
| 5,891,140 A | 4/1999 | Ginn et al. |
| 5,919,191 A | 7/1999 | Lennox et al. |
| 5,955,514 A | 9/1999 | Huang et al. |
| 5,964,968 A | 10/1999 | Kaneko |
| 6,032,077 A | 2/2000 | Pomeranz |
| 6,033,654 A | 3/2000 | Stedronsky et al. |
| 6,086,585 A | 7/2000 | Hovda et al. |
| 6,112,122 A | 8/2000 | Schwardt et al. |
| 6,113,596 A | 9/2000 | Hooven et al. |
| 6,117,109 A | 9/2000 | Eggers et al. |
| 6,135,998 A | 10/2000 | Palanker |
| 6,149,620 A | 11/2000 | Baker et al. |
| 6,159,194 A | 12/2000 | Eggers et al. |
| 6,162,219 A | 12/2000 | Nilsson et al. |
| 6,174,309 B1 | 1/2001 | Wrublewski et al. |
| 6,206,878 B1 | 3/2001 | Bishop et al. |
| 6,207,134 B1 | 3/2001 | Fahlvik et al. |
| 6,213,999 B1 | 4/2001 | Platt et al. |
| 6,214,003 B1 | 4/2001 | Morgan et al. |
| 6,224,592 B1 | 5/2001 | Eggers et al. |
| 6,235,024 B1 | 5/2001 | Tu |
| 6,241,723 B1 | 6/2001 | Heim et al. |
| 6,241,753 B1 | 6/2001 | Knowlton |
| 6,264,650 B1 | 7/2001 | Hovda et al. |
| 6,264,652 B1 | 7/2001 | Eggers et al. |
| 6,273,883 B1 | 8/2001 | Furumoto |
| 6,293,942 B1 | 9/2001 | Goble et al. |
| 6,306,134 B1 | 10/2001 | Goble et al. |
| 6,309,387 B1 | 10/2001 | Eggers et al. |
| 6,322,549 B1 | 11/2001 | Eggers et al. |
| 6,350,276 B1 | 2/2002 | Knowlton |
| 6,383,184 B1 | 5/2002 | Sharkey |
| 6,391,025 B1 | 5/2002 | Weinstein et al. |
| 6,416,509 B1 | 7/2002 | Goble et al. |
| 6,419,815 B1 | 7/2002 | Chambers et al. |
| 6,461,352 B2 | 10/2002 | Morgan et al. |
| 6,463,336 B1 | 10/2002 | Mawhinney |
| 6,471,993 B1 | 10/2002 | Shastri et al. |
| 6,547,794 B2 | 4/2003 | Auge |
| 6,558,382 B2 | 5/2003 | Jahns et al. |
| 6,743,248 B2 | 6/2004 | Edwards et al. |
| 6,772,013 B1 | 8/2004 | Ingle et al. |
| 6,780,178 B2 | 8/2004 | Palanker et al. |
| 6,824,555 B1 | 11/2004 | Towler et al. |
| 6,832,995 B1 | 12/2004 | Towler et al. |
| 6,890,332 B2 | 5/2005 | Truckai et al. |
| 6,902,564 B2 | 6/2005 | Morgan et al. |
| 7,066,932 B1 | 6/2006 | Morgan et al. |
| 7,105,011 B2 | 9/2006 | Auge |
| 7,354,438 B2 | 4/2008 | Morgan et al. |
| 7,445,619 B2 | 11/2008 | Auge et al. |
| 7,549,989 B2 | 6/2009 | Morgan et al. |
| 7,713,269 B2 | 5/2010 | Auge et al. |
| 7,771,422 B2 | 8/2010 | Auge et al. |
| 7,819,861 B2 | 10/2010 | Auge et al. |
| 7,819,864 B2 | 10/2010 | Morgan et al. |
| 2001/0007940 A1 | 7/2001 | Tu et al. |
| 2002/0165596 A1 | 11/2002 | Wilson |
| 2002/0183737 A1 | 12/2002 | Kristensen |
| 2003/0028189 A1 | 2/2003 | Woloszko et al. |
| 2003/0036753 A1 | 2/2003 | Morgan et al. |
| 2003/0216732 A1 | 11/2003 | Truckai et al. |
| 2003/0216733 A1 | 11/2003 | McClurken et al. |
| 2004/0082945 A1 | 4/2004 | Clague et al. |
| 2004/0167244 A1 | 8/2004 | Auge, II |
| 2004/0267255 A1 | 12/2004 | Auge, II et al. |
| 2005/0085806 A1 | 4/2005 | Auge, II et al. |
| 2005/0182449 A1 | 8/2005 | Auge, II et al. |
| 2009/0030410 A1 | 1/2009 | Auge, II et al. |
| 2009/0306645 A1 | 12/2009 | Morgan et al. |
| 2010/0069975 A1 | 3/2010 | Auge et al. |
| 2010/0087815 A1 | 4/2010 | Morgan et al. |
| 2011/0087308 A1 | 4/2011 | Morgan et al. |

FOREIGN PATENT DOCUMENTS

| | | |
|---|---|---|
| WO | WO-02/102438 | 12/2002 |
| WO | WO-03/015865 | 2/2003 |

| WO | WO-03103522 | 6/2003 |
| WO | WO-03/103521 | 12/2003 |
| WO | WO-2011047148 | 4/2011 |

OTHER PUBLICATIONS

Brennetot, R. et al., "Investigation of Chelate Formation, Intramoecular Energy Transfer and Luminescence Efficiency and Lifetimes in the Euthenoyltrifluoroacetone-trioctylphosphine oxide-Triton x-100 System Using Absorbance, Fluorescence and Photothermal Measurements", *Spectrochim ACTA A Mol. Biomol. Spectrosc., Part A-56*, 2000, pp. 702-715.

Chen, S. S., et al., "Heat-Induced Changes in the Mechanics of a Collagenous Tissue: Isothermal, Isotonic Shrinkage", *Transactions of the ASME* vol. 120, 1998, pp. 382-388.

Edwards, R B., et al., "Thermometric determination of cartilage matrix temperatures during thermal chondroplasty: comparison of bipolar and monopolar radiofrequency devices", *Arthroscopy* Apr. 2000;18(4), pp. 339-346.

Fink, Bernd, et al., "Holmium: YAG Laser-Induced Aseptic Bone Necroses of the Femoral Condyle", *Arthroscopy: The Journal of Arthroscopic and Related Surgery* vol. 12 No. 2, 1996, pp. 217-223.

Gould, Stephen E., et al., "Cellular Contribution of Bone Graft to Fusion", *Journal of Orthopaedic Research* vol. 18, 2000, pp. 920-927.

Grant, Kyle M., et al ""Magnetic Field-Controlled Microfluidic Transport"", *Journal of American Chemical Society (JACS) Articles*, vol. 124. No. 3, 2002, pp. 462-467.

Ito, Takayasu, et al., "Sensitivity of Osteoinductive Activity of Deminerlization and Defatted Rat Femur to Temperature and Duration of Heating", *Clinical Orthopaedics and Related Research* No. 316, 1995, pp. 267-275.

Janzen, Dennis L. et al., "Osteonecrosis After Contact Neodymium: Yttrium Aluminum Garnet Arthroscopic Laser Meniscectomy", *AJR* 169 1997, 855-858.

Lopez, Mandi J. et al., "Effects of Monopolar Radiofrequency Energy on Ovine Joint Capsular Mechanical Properties", *Clinical Orthopaedics and Related.Research*, No. 374, 2000, pp. 286-297.

Medvecky, Michael J., et al., "Thermal Capsular Shrinkage: Basic Science and Clinical Applications", *Arthroscopy*, 2001, vol. 17, no. 6, Jul. 2001, pp. 624-635.

Minczykowski, Andrzej, et al., "Effects of Magnetic Resonance Imaging on Polymorphonuclear Neutrophil Adhesion", Diagnostics and Medical Technolgy, *Medical Science Monitor*, vol. 7(3), 2001, pp. 482-488.

Mourant, Judith R., et al., "Improvements in Laser "Welding" of Chicken Bone Tibias in vitro", *Laser Sciences and Applications Group*, Los Alamos, NM, pp. 1-8.

Mourant, Judith R., et al., "Laser Welding of Bone: Successful in vitro Experiments", *Laser Sciences and Applications Group*, Los Alamos, NM, pp. 1-5.

Rozbruch, S. R., et al., "Osteonecrosis of the Knee Following Arthroscopic Laser Meniscectomy", *Arthroscopy: The Journal of Arthroscopic and Related Surpery* vol. 12 No. 2, 1996, pp. 245-250.

Thal, Raymond, et al., "Delayed Articular Cartilage Slough: Two Cases Resulting From Holmium: YAG Laser Damage to Normal Articular Cartilage and a Review of the Literature", *Arthroscopy: The Journal of Arthroscopic and Related Surgery* vol. 12 No. 1, 1996, pp. 92-94.

Torchilin, Vladimir P., "Drug Targeting", *European Journal of Pharmaceutical Sciences*, vol. 11, Supplement 2, 2000, pp. S81-S91.

Wall, Michael S., et al., "Thermal Modification of Collagen", *J. Shoulder Elbow Surg.* vol. 8 No. 4, 1999, pp. 339-344.

Wallace, Andrew L., et al., "Electrothermal Shrinkage Reduces Laxity but Alters Creep Behavior in a Lapine Ligament Model", *J. Shoulder Elbow Surg.* vol. 10 No. 1, 2001, pp. 1-6.

Zhang, Min, et al., "Effects of the Demineralization Process on the Osteoinductivity of Demineralized Bone Matrix", *J. Periodontaol*, vol. 68 No. 11, Nov. 1997, pp. 1085-1092.

Zohar, Ofer, et al., "Thermal Imaging of Reeptor-Activated Heat Production in Single Cells", *Biophysical Journal*, vol. 74, Jan. 1998, pp. 82-89.

INTERFACING MEDIA MANIPULATION WITH NON-ABLATION RADIOFREQUENCY ENERGY SYSTEM AND METHOD

CROSS-REFERENCE TO RELATED APPLICATIONS

This application is a continuation-in-part application of U.S. patent application Ser. No. 12/580,195 entitled "Electrosurgical Plenum", to Roy E. Morgan and Wayne K. Augé, II, filed on Oct. 15, 2009, and which itself is a continuation-in-part application of U.S. patent application Ser. No. 12/479,578, entitled "Electrosurgery Devices", to Roy E. Morgan and Wayne K. Augé, II, filed on Jun. 5, 2009, and issued on Oct. 26, 2010 as U.S. Pat. No. 7,819,864, which itself is a divisional of U.S. patent application Ser. No. 11/847,216, entitled "Electrosurgery Devices", filed on Aug. 29, 2007, and issued on Jun. 23, 2009 as U.S. Pat. No. 7,549,989, which itself is a divisional of U.S. patent application Ser. No. 11/147,481, entitled "Devices for Electrosurgery", filed on Jun. 7, 2005, and issued on Apr. 8, 2008 as U.S. Pat. No. 7,354,438, which itself is a divisional of U.S. patent application Ser. No. 10/119,671, entitled "Methods and Devices for Electrosurgery", filed on Apr. 9, 2002, and issued Jun. 7, 2005 as U.S. Pat. No. 6,902,564, which itself claims priority to U.S. Provisional Patent Application Ser. No. 60/312,965, filed on Aug. 15, 2001, and the specification and claims thereof are incorporated herein by reference. This application is also a continuation-in-part application of U.S. patent application Ser. No. 12/486,616, entitled "Active Conversion of a Monopolar Circuit to a Bipolar Circuit Using Impedance Feedback Balancing", to Roy E. Morgan and Wayne K. Augé, II, filed on Jun. 17, 2009, and the specification and claims thereof are incorporated herein by reference. This application is also a continuation-in-part application of U.S. patent application Ser. No. 11/006,079, entitled "Methods and Devices for Electrosurgery", filed Dec. 6, 2004 and issued on Aug. 10, 2010 as U.S. Pat. No. 7,771,422, which is a continuation-in-part application of PCT/US03/018116 entitled "Methods and Devices for Electrosurgery", filed on Jun. 6, 2003, which itself claims priority to and the benefit of the filing of U.S. Provisional Patent Application Ser. No. 60/387,775, entitled "Methods and Devices for Electrosurgery and Electrolysis", filed Jun. 10, 2002 and which claims priority to and the benefit of the filing of U.S. Provisional Patent Application Ser. No. 60/387,114, entitled "Methods and Devices for Electrosurgery", filed Jun. 6, 2002, and the specifications and claims (if any) thereof are incorporated herein by reference.

BACKGROUND

Surgical devices that deploy an electrical circuit between electrodes do so in an electrically conductive medium, which may be either in vivo biologic tissues or delivered media such as electrolyte solutions. The tissue effects produced by these devices are dependent upon the events occurring at or around the electrodes as electrical energy is converted to therapeutically useful forms. Converted energy forms can be either near-field at the electrode surface or far-field projected away from the electrodes. Near-field effects are produced by electrical current and include physiochemical events like electrothermal and electrochemical conversions; far-field effects are produced by electromagnetic radiation forces like magnetic flux densities, voltage potentials, or displacement currents generated around the electrodes. Gross electrical conduction in biological tissues is principally due to the conductivity of in situ interstitial fluids which are electrolyte water-based and thus predominantly ionic. Since the electrical charge carriers in metal electrodes are primarily electrons, the transition between electronic and ionic conduction is governed by physiochemical processes at the electrode-to-fluid interface within the conductive media, even though this process can be altered by electrode contact with macromolecular biologic material. Electrically conductive media solutions have been used for many decades to complete surgical device circuits and no longer alone serve as a proprietary method of circuit completion (Elässer E, Roos E. Uber ein instrument zur leckstromfreien transurethralen resektion [An instrument for 440 transurethral resection without leakage of currents]. Acta Medico Technica. 1976; 24(4):129-134). Both direct current and alternating current formulations have been deployed in surgical device designs.

Surgical use of direct current induces tissue necrosis as a means to destroy unwanted tissue through near-field electrical current effects delivered into biologic structures. Electrolytic ablation, or tissue electrolysis, is a technique which consists of placing an anode electrode and cathode electrode at various points within or adjacent to tissue and driving direct current (40-100 mA) between them and through the biologic mass to induce tissue electrolysis. The products of tissue electrolysis kill cells by creating, in a spherical area surrounding the each electrode, local changes in tissue pH too large for cells to survive. These pH changes are caused by creating toxic products such as chlorine, oxygen, and hydrogen ions at the anode electrode and hydrogen gas and sodium hydroxide at the cathode electrode. The region surrounding the anode becomes very acidic (~pH 2) and surrounding the cathode becomes strongly alkaline (~pH 12) with the amount of necrosis dependent upon the total electrolysis dose measured in coulombs as a product of tissue current delivery and time. A pH less than 6.0 at the anode and greater than 9.0 at the cathode reflects total cellular necrosis. Direct current applications deliver static electromagnetic fields that have inconsequential quanta in the regions of non-necrotic tissue. Electrolytic ablation does not rely upon a thermal effect as tissue temperatures only rise minimally during these procedures to levels not associated with cell death.

Surgical use of alternating current has been designed to induce therapeutic necrosis for volumetric tissue removal, coagulation, or dissection through near-field electrical current effects within biologic tissues. Radiofrequency wavelengths and frequencies do not directly stimulate nerve or muscle tissue; and, so are prevalent in medical applications. Radiofrequency surgical devices utilize tissue as the primary medium like in direct current applications; however, these surgical devices produce resistive tissue heating (ohmic or Joule heating) by an alternating current induced increase in molecular kinetic or vibrational energy to create thermal necrosis. In order to obtain the desired levels of thermal necrosis through resistive heating in a media with exceptionally large specific heat capacity such as water found in and around biologic tissues, high-levels of alternating current deposition are required to maintain heat production, and conduction to remote tissue, in the presence of treatment site thermal convection. In certain settings, high-level energy radiofrequency devices can be configured to produce water vapor preferentially through very rapid and intense resistive heating, overcoming the high heat of vaporization at the treatment site. Coincident with this method, the far-field time-varying electromagnetic forces of these devices deliver quanta able to generate charged plasma particles within the water vapor cloud. This ionizing electromagnetic radiation can induce an electron cascade, which operates over very short distances (Debye sphere) and with electron temperatures of several thousand degrees Celsius, to produce therapeutic molecular disintegration of biologic tissues as its action decays into heat. Radiofrequency thermal ablation and plasma-based techniques display use limitations associated with their design. Thermal and plasma lesions spread according to induced gradients; but, because of the variable energy transfer coefficients in the treatment settings of biologic tissues, iatrogenic tissue charring, necrosis, and collateral damage from imprecise heating or excess energy deposition can occur.

Electrolytic ablation, radiofrequency thermal ablation, and radiofrequency plasma-based surgical devices are designed for a direct electrode-to-tissue interface, concentrating near-field electrical energy to perform surgical work centered upon therapeutic necrosis. In these applications, collateral damage is a normal procedural consequence since the application locales to which these devices are deployed can often accommodate an excess or imprecise application of energy to ensure expedient procedural efficacy within varying treatment site conditions.

From a surgical work energy procurement standpoint, these procedures are defined by an inefficient use of electrical energy due to the excess energy deposition that occurs within biologic tissue producing iatrogenic collateral damage. Far-field electromagnetic forces, although present, are confounded by tissue current deposition or, in the case of plasma-based radiofrequency devices, are of such a high intensity constituting local ionizing electromagnetic radiation. Electrolytic ablation, radiofrequency thermal ablation, and radiofrequency plasma devices all struggle in balancing volumetric tissue removal with healthy tissue loss because of excess collateral energy deposition into the tissue.

BRIEF DESCRIPTION OF THE INVENTION

One embodiment of the present invention provides a method for inducing a therapeutic response in living tissue while minimizing current deposition in living tissue, the method comprising providing a probe to an aqueous salt ion solution of a treatment site where a therapeutic response in living tissue is desired wherein the probe includes an active electrode and a return electrode separated by an insulator and wherein the living tissue is separated from the active electrode by a plenum housing the active electrode; immersing of at least the portion of the probe and plenum including the active electrode and the return electrode in the aqueous salt ion solution; positioning the plenum housing the active electrode in close proximity to the treatment site, the active electrode and return electrode being immersed in the aqueous salt ion solution; and applying a high voltage potential between the electrodes to deliver an electromagnetic non-ionizing radiation to the living tissue at the treatment site to induce a therapeutic response in the living tissue.

In a preferred embodiment, the therapeutic response is activation of tissue voltage sensor domains, stress response gene expression, and direct voltage-to-force energy conversion molecular motors, and cell proliferation.

In another preferred embodiment the high voltage potential between the active electrode and return electrode does not create temperatures to cause water vapor as the current applied to generate the high voltage potential is below that to cause water vapor when acting in an aqueous environment. In yet another preferred embodiment applying a high voltage potential between the electrodes in the aqueous salt ion solution generates a redox magnetohydrodynamic fluid flow that recharges reactants near the active electrode located within the plenum and wherein the plenum vents the fluid flow to the treatment site. In yet another preferred embodiment the method further comprising treating tissue at a treatment site with reactants from the redox magnetohydrodynamic fluid flow reaction as a result of creating a high voltage potential between the active and return electrode of a device as described. In a preferred embodiment the plenum protects a primary reaction zone from convective forces at the treatment site.

Another embodiment provide for a method of performing an electrosurgical procedure on a patient to produce a therapeutic response, the method comprising providing a surgical probe including an active electrode and a return electrode separated by an insulator wherein the active electrode is located with a plenum of the device; providing an aqueous salt ion environment at the location wherein the electrosurgical procedure is to be performed, the environment comprising sufficient volume to permit immersion of at least the portion of the surgical probe including the active electrode within the plenum and the return electrode; and applying current to a circuit comprising the active electrode and return electrode, the current being less than that required to induce plasma ionization, but sufficient to induce a repetitive molecular energy conversion loop from a portion of the aqueous salt ion environment to produce a therapeutic response at the treatment site.

In a preferred embodiment the therapeutic response is a healing response. In yet another preferred embodiment the healing response comprises one or more of the following: activation of tissue voltage sensor domains, stress response gene expression, direct voltage-to-force energy conversion molecular motors activation, and cell proliferation. In yet another preferred embodiment the method further comprising concentrating and or enriching the reactants or products of the repetitive molecular energy conversion loop in an aqueous environment for therapeutic use at a treatment site with the plenum. In a preferred embodiment the plenum protects a primary reaction zone from convective forces of the surgical site.

Another embodiment provides for a non-ablation device for applying energy to a treatment site on living tissue during electrosurgery of a subject comprising an active electrode electrically coupled to an electric current power supply. The electrode is positionable in close proximity to the treatment site in the presence of an electrolyzable fluid and separated from the treatment site by a plenum attached to the non-ablation device and an electric current power supply for generating a voltage potential between the active electrode and a return electrode, the voltage potential being sufficient to create a non-ionizing electromagnetic field to induce a non-ablation therapeutic response in the tissue.

In a preferred embodiment the plenum contains vents in a side to provide a current density that is dispersed into an interfacing media via vents in the plenum for indirect treatment of living tissue (i.e. no direct contact of the active electrode with the living tissue at the treatment site). In yet another preferred embodiment the non-ablation device limits tissue electrolysis and resistive heating from current.

Another embodiment provides for a method of treating living tissue with a device according to the above described device comprising treating living tissue with near field effects and far field effects simultaneously wherein the near field effects and the far field effects can be segregated with a vented plenum that separates the active electrode from the living tissue at the treatment site.

The effects of non-ablative radiofrequency energy deposition upon interfacing media typically encountered during surgical applications and systems and methods for utilizing the same in a therapeutic setting is disclosed according to at least one embodiment of the present invention.

One aspect of one embodiment of the present invention provides a non-ablation radiofrequency device which does not rely upon a direct electrode-to-tissue interface to treat the tissue at the treatment site.

Another aspect of one embodiment the present invention provides a system and method for providing therapeutic treatment of living tissue having a near-field effect on the interfacing medium and a far-field effect which can be delivered into biologic tissue simultaneously or independently during tissue treatment.

One aspect of one embodiment of the present invention provides a method of delivering electromagnetic non-ionizing radiation to tissue at or near a site targeted for treatment which distance is for example of about 0.01 mm to about 3 mm and is determined by the plenum.

Another aspect of the one embodiment of the present invention provides a method of delivering current from an active electrode to an interfacing medium to produce an energy conversion event wherein the energy conversion event (i.e. ionic species, acid-base shifts, electrothermal, electrochemical, and physiochemical conversions) is dispersed to the treatment site through vents in or a throttling mechanism of the plenum of the device.

Another aspect of one embodiment of the present invention provides an electrosurgical non-ablation device wherein the energy conversion event is dispersed to the treatment site through vents in or a throttling mechanism of the plenum of the device.

Another aspect of one embodiment of the present invention provides high voltage potentials between the active and the return electrodes to provide a method of treatment to a living tissue at the treatment site in the absence of high current.

Another aspect of one embodiment of the present invention provides a device having an electrode architecture based upon voltage potential disparities rather than current density disparities.

Another aspect of one embodiment of the present invention provides a method of treating living tissue with near field effects and far field effects simultaneously wherein the near field effects and the far field effects can be segregated with an electrosurgical plenum that separates the active electrode from the living tissue at the treatment site.

Another aspect of the one embodiment of the present invention provides a device comprising a plenum wherein a current density is dispersed into an interfacing media via vents in or a throttling mechanism of the plenum for indirect treatment of living tissue (i.e. no direct contact of the active electrode with the living tissue at the treatment site).

Another aspect of one embodiment of the present invention provides a non-ablation device that limits tissue electrolysis and resistive heating from current.

Another aspect of one embodiment of the present invention provides a device that utilizes a repetitive molecular energy conversion loop (RMECL) to produce reactive species (i.e. electrothermal, electrochemical, and/or physiochemical) that are delivered to the target site of the living tissue.

Another aspect of one embodiment of the present invention provides that the high voltage potential between the active electrode and return electrode does not create temperatures to cause water vapor as the current applied is below that to cause water vapor when acting in an aqueous environment.

Another aspect of one embodiment of the present invention provides a device that concentrates and or enriches the reactants or products of the RMECL within the plenum in an aqueous environment for therapeutic use at a treatment site of living or nonliving (de-vitalized) tissue.

Another aspect of one embodiment of the present invention provides for a method of treating living tissue at a treatment site by generating a redox magnetohydrodynamic fluid flow to recharge reactants near the active electrode and vent the fluid flow with a plenum to the treatment site.

Another aspect of one embodiment of the present invention provides a method for treating tissue at a treatment site with reactants from a redox reaction as a result of creating a high voltage potential between a active and return electrode of a device as described.

Another aspect of one embodiment of the present invention provides electrosurgical plenum protects the (i.e. within the plenum chamber) primary reaction zone from convective forces of the surgical site Aspects, advantages and novel features, and further scope of applicability of embodiments of the present invention will be set forth in part in the detailed description to follow, taken in conjunction with the accompanying drawings, and in part will become apparent to those aspects and advantages of embodiments of the present invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 5 A: Two half-reactions of the thermochemical cycle that describe the quantitative relationships between the reactants and products for the Repetitive Molecular Energy Conversion Loop.

FIG. 5 B: With loss of reactants or products from the primary reaction zone, such as gas emanation modulated by the protective housing throttling vent/plenum, the electrochemical effects can become more visible. These electrochemical effects are termed an acid-base shift.

FIG. 5 C: A more general case in which the ionic salt is represented by variable X, where X is any appropriate group 1, period 1-7 element of the periodic table. The salt-bridge catalytic efficiency is dependent upon the salt's elemental properties.

FIG. 5 D: The Repetitive Molecular Energy Conversion Loop is demonstrated by variables consisting of $\alpha$, $\beta$, $\gamma$, and $\delta$400 wherein, the molar quantities required are any value that appropriately satisfies the oxidation reduction valence requirements for the overall reaction.

DETAILED DESCRIPTION OF THE INVENTION

Newer surgical uses of alternating current include non-ablation radiofrequency systems which deliver low-level energy to tissues through a protective tip architecture that prevents active electrode-to-tissue contact and therefore do not rely upon a direct electrode-to-tissue interface. The protected electrode allows a more controlled and directed energy delivery to modify or precondition tissue allowing tissue preservation even during resection or debridement applications. Because the electrodes do not contact tissue during activation, electrical current deposition is concentrated into an interfacing media within the protective housing rather than directly into and through biologic tissue as in ablation-based devices. The protective housing provides the ability to move, manipulate, and segregate the near-field effects both tangentially and perpendicularly to the tissue surface during modification or preconditioning; and, it can serve as a mechanical implement and selective throttling vent/plenum during use. For example, the near-field effects are often configured to match current density dispersion with biologic tissue surfaces in a procedure-specific manner. This design allows more consistent electrical current near-field effects at the electrode surface because the circuit is not required to accommodate widely fluctuating impedance changes that tissue contacting electrodes create. Accordingly, tissue electrolysis and resistive (ohmic or Joule) tissue heating can be prevented. These devices allow a more efficient surgical work energy procurement as iatrogenic collateral tissue damage is minimized without compromising procedural efficacy. Non-ablation devices can deliver useable far-field electromagnetic forces to surface and subsurface tissues designed to create quantitatively and qualitatively larger strengths in tissue not damaged by excessive current deposition or ionizing electromagnetic radiation. These devices are used to permit normal tissue healing responses during modification and preconditioning through segregated near-field effects, while creating far-field electromagnetic intensities designed to induce tissue healing responses within the preserved tissue not subjected to collateral damage.

Figure 1:
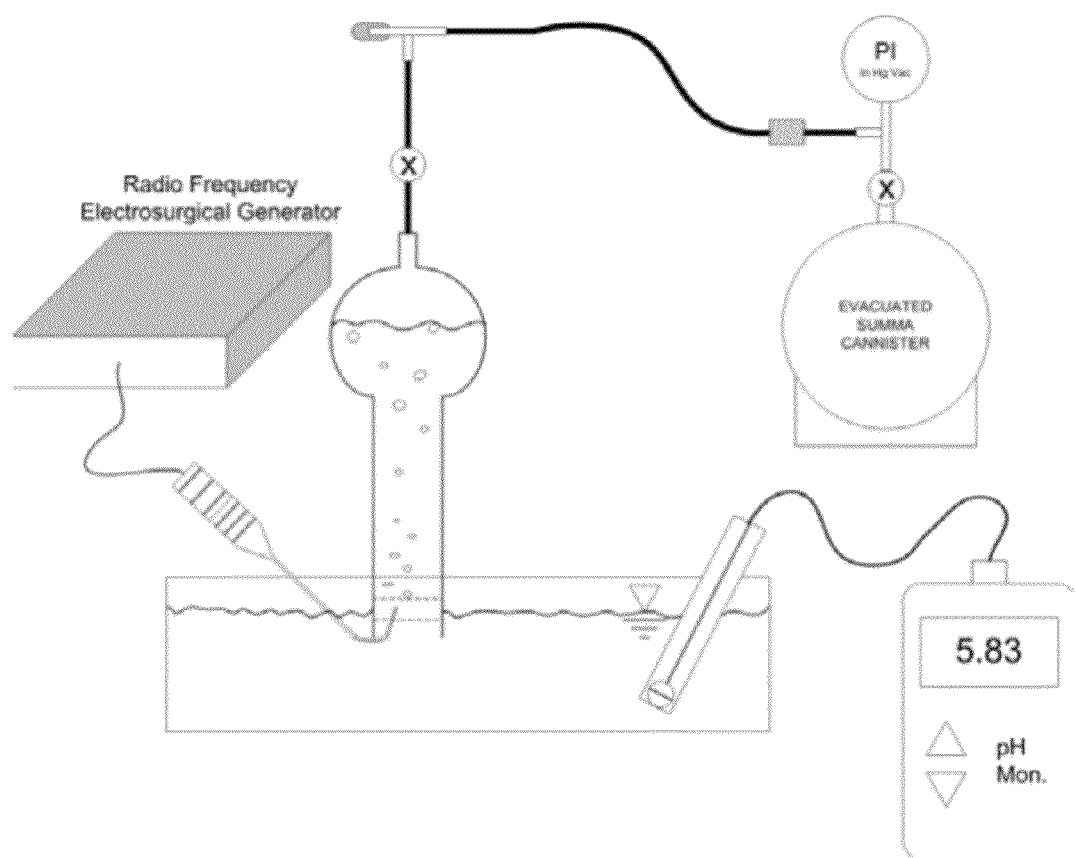
FIG. 1: Experimental laboratory set-up designed to evaluate the near-field effects of non-ablative radiofrequency manipulation of saline interfacing media.
Figure 2:
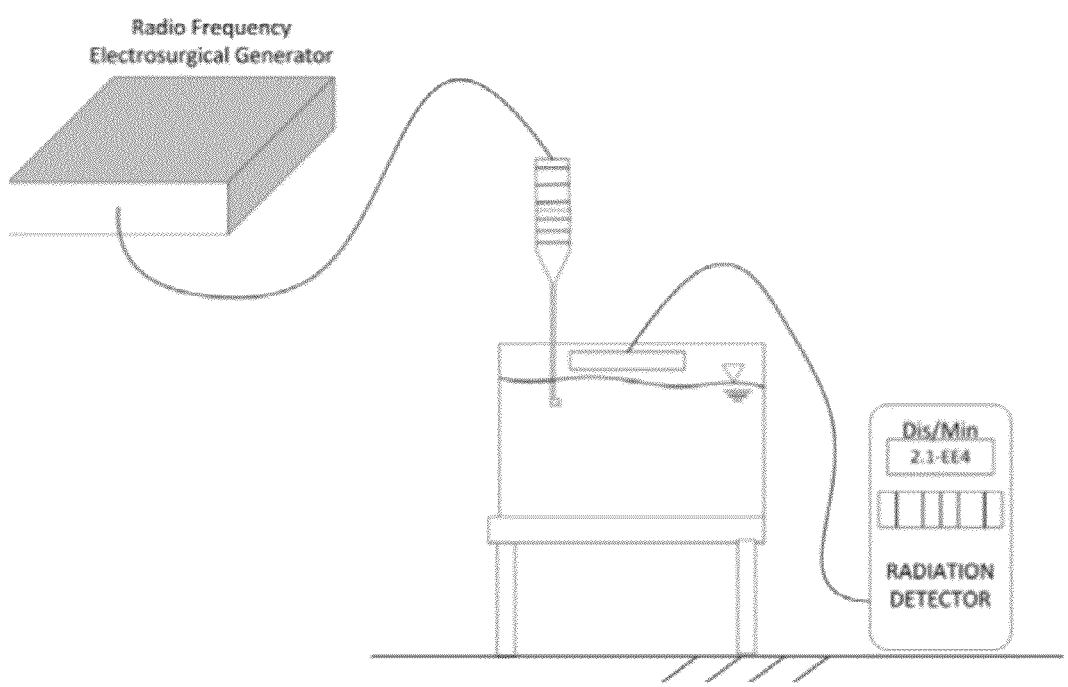
FIG. 2: Experimental laboratory set-up designed to determine whether generation of charged particles occurs with non-ablative radiofrequency manipulation of saline interfacing media. The distances between the electrode and the water surface are exaggerated for purposes of illustration.
Figure 3:
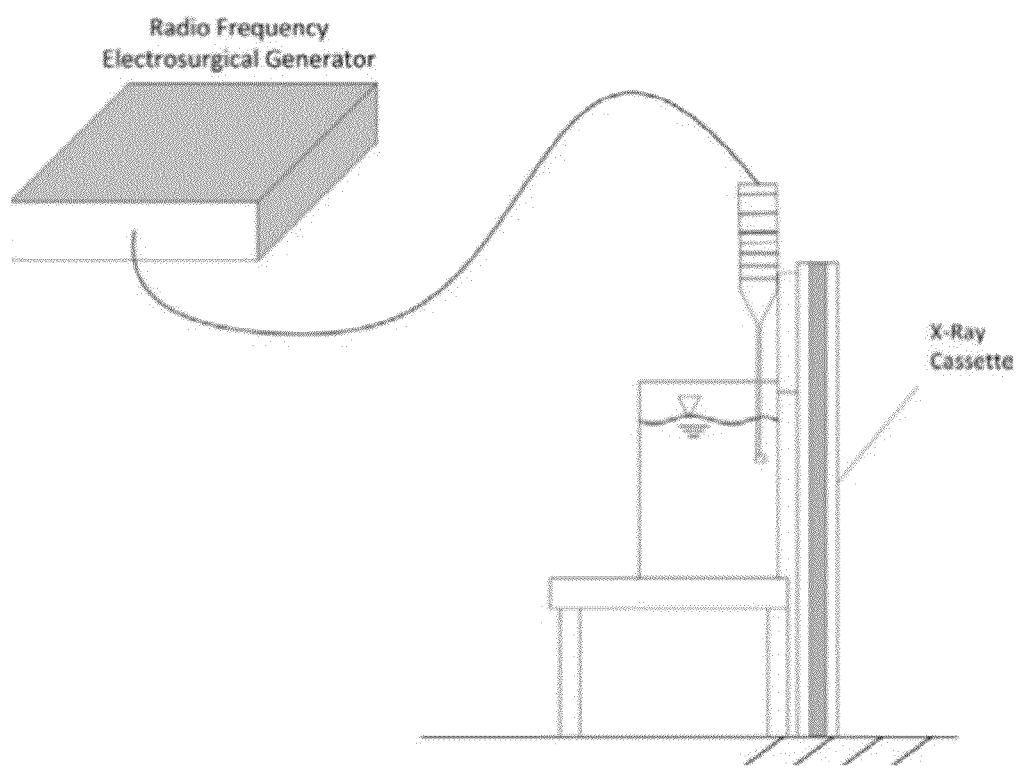
FIG. 3: Time integrated experimental laboratory set-up designed to determine whether generation of charged particles occurs with non-ablative radiofrequency manipulation of saline interfacing media.

Radiofrequency surgical devices were tested in the apparatuses depicted in FIGS. 1-3 with baseline interfacing media typically used during surgical applications and consisting of 0.9% sodium chloride at 300 mOsm/L at 200 C. The surgical devices were comprised of stainless steel metal electrodes containing a small amount of titanium (0.5%) used to stabilize its structure at higher temperatures, to prevent carbide precipitation from the grain boundaries, and to protect the metal from corrosion. The protective housing was comprised of an electrical and thermal insulating ceramic designed to prevent electrode-to-tissue contact. The surgical devices were configured in a bipolar fashion connected to an electrosurgical generator delivering radiofrequency energy at varying power outputs (0-350 W), voltage potentials (0.1-4.5 kV), and frequencies (100 kH-1 MH). A general characteristic of non-ablation radiofrequency energy is a low current density bias and a high voltage potential bias.

FIG. 1 apparatus was designed to evaluate the near-field effects of non-ablation radiofrequency energy that occur within the protective tip housing (primary reaction zone). Interfacing media salt concentration and energy configuration delivered were varied to determine their relationship to temperature and pH changes of the interfacing media in the primary reaction zone. These assessments were correlated with the production of non-soluble gas. When gas production occurred, gas generation dynamics were characterized by video assessment and digitization and compared to the water vapor bubble production typical of ablation-based radiofrequency devices. Gas was collected for gas chromatography and mass spectrometry evaluations of constituent species. A separate container of collected gas was allowed to stand at ambient conditions to determine condensation behavior.

The gas collection process included an inverted glass collection tube fully filled with the same interfacing media as in the reaction reservoir to create a manometer fluid column that could be displaced by collected gas. Generated gas bubbles were allowed to naturally float into the capture section of collecting tube via buoyancy forces to displace approximately 95% of its total volume. Thereafter, the gas was evacuated from the collection tube by partially opening the stopcock valve to form a restriction and then sequentially opening the needle valve allowing the gas to fill the summa canister. The combined flow restrictions allowed inlet gas rate metering to avoid unwanted water uptake into the summa canister. The summa canister was allowed to maintain an intact partial vacuum with an attached pressure gauge so that the receiving laboratory could verify whether inadvertent uptake of contaminating atmosphere had occurred during transport.

FIG. 2 apparatus was designed to evaluate the far-field effects of non-ablation radiofrequency energy at distances typical for the edge of the protective tip housing and within the electromagnetic fields generated by the surgical device. The production of ionizing electromagnetic radiation was monitored using a radiation and particle detector in the treatment field sensitive to 200 disintegrations per minute at 1 mm distance from the air-water interface, a distance over which a 0.5 keV particle would be transmitted as the removal of shell electrons emits characteristic energies from a few keV to over 100 keV. This sequential phase interface design allowed particles to be detected if produced in any appreciable quantity above normal background radiation.

FIG. 3 apparatus was designed to time integrate roentgenographic film exposure by particle generation. The surgical device was fully immersed and placed with the active electrode within 1 mm of the glass wall of the reservoir and activated for a continuous 30 minutes allowing any ionized reaction zone species to integrate over time and expose the film. A control source of alpha ($\alpha$) particles was adhesively affixed to the glass wall to demonstrate time dependant control exposure.

Figure 4:
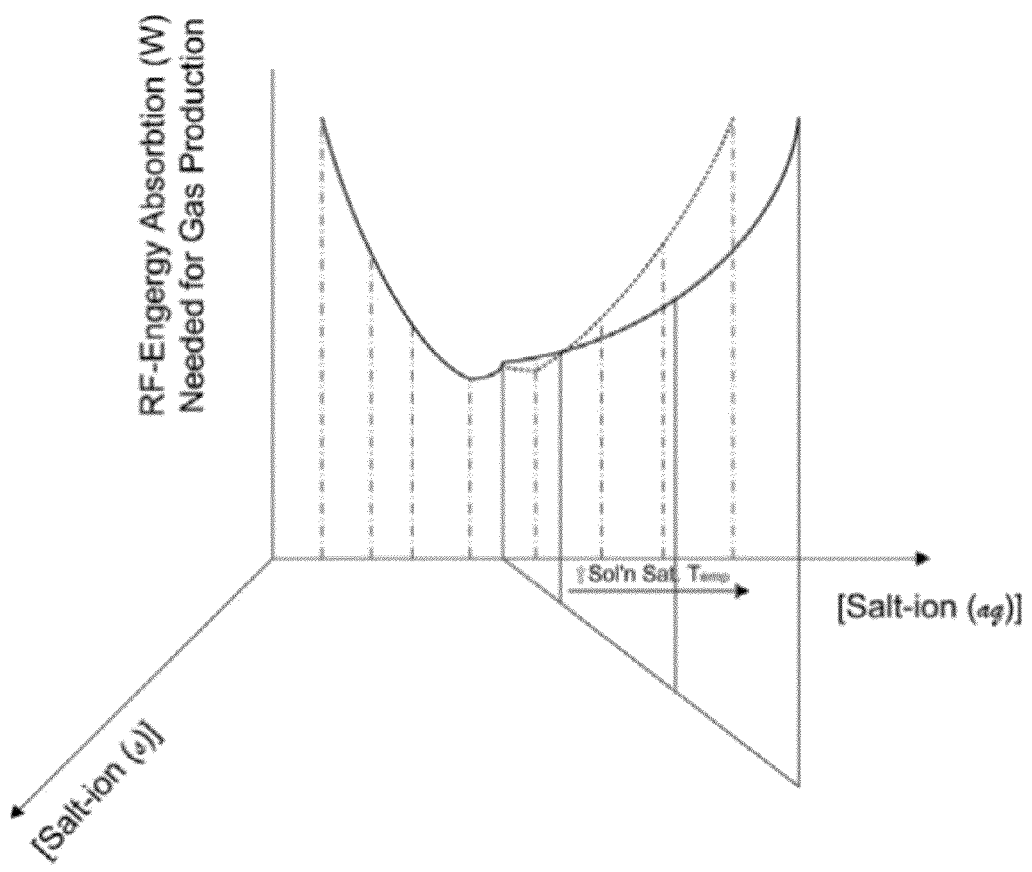
FIG. 4: Graphic representation of the manipulation of saline interfacing media by non-ablative radiofrequency energy depicting the general energy absorption curves which follow non-linear mathematical relationships. The curves depicted show the multi-dimensional aspects of the immersed environment and how they affect the overall process including solution temperature.
Figure 5A:
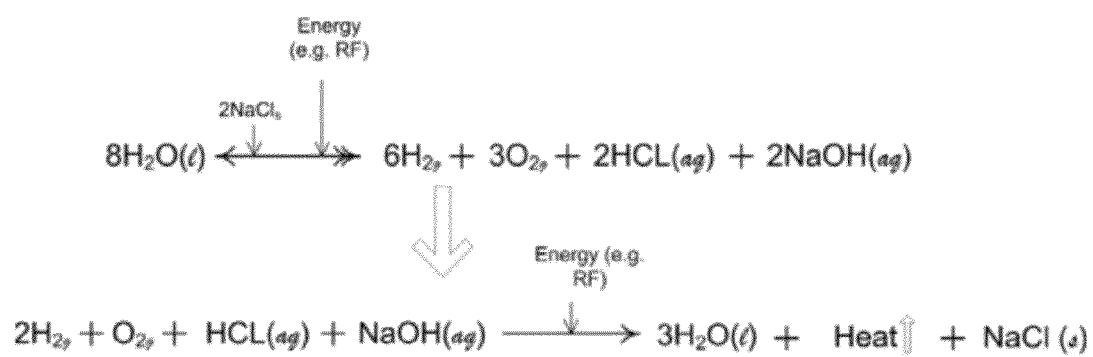
FIG. 5: Reaction stoichiometry of the near-field effects of non-ablative radiofrequency manipulation of saline interfacing media.
Figure 5B:
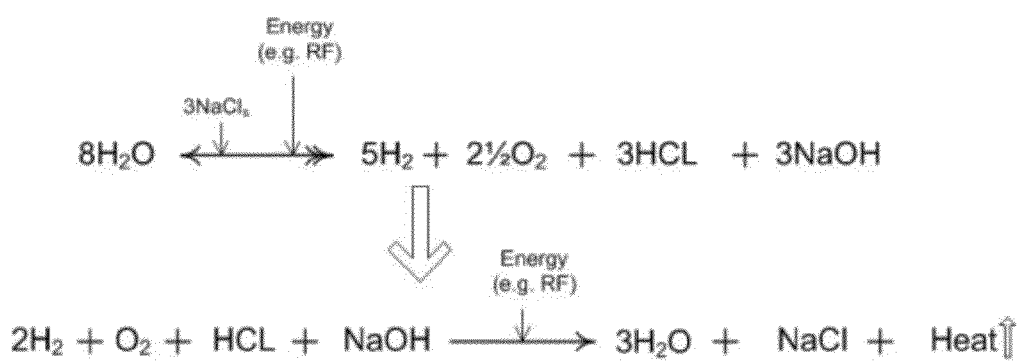
Figure 5C:
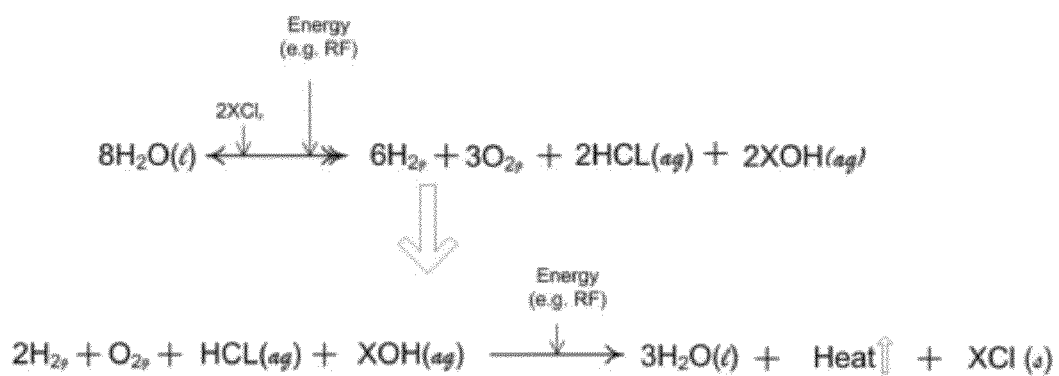
Figure 5D:
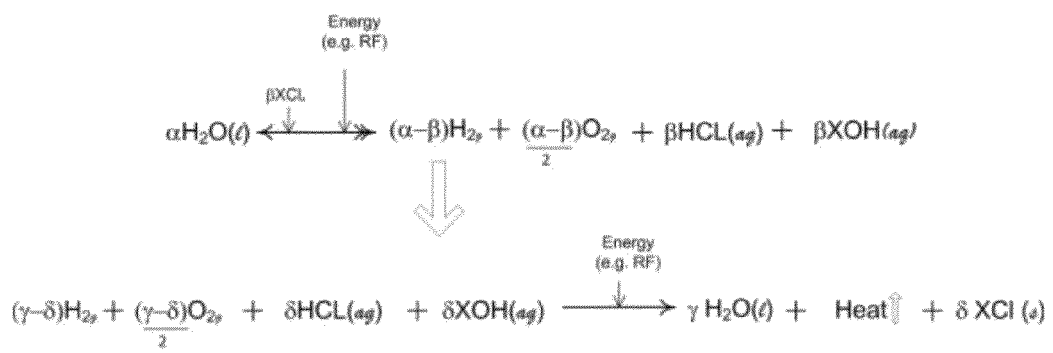

Near-Field Characterization
General Observations:

Two non-ablation radiofrequency energy conversion modes were evident based upon visual cues that can be used to define surgical work: one during which the device deploys energy levels that do not produce non-soluble gas; the other during which non-soluble gas is produced. These modes were part of an observable continuum that 7 was modifiable based upon salt concentration of and energy applied to the interfacing media as depicted in FIG. 4. Characteristic temperature and pH changes within the primary reaction zone occurred commensurate with near-field energy delivery level.

Electrothermal Effects:

Electrothermal effects were present during both modes of operation. Heat was generated well below the level at which water vapor could be produced. The thermal gradients migrated from the electrode based upon typical thermodynamic behavior but could be altered by the configuration of the protective housing.

Electrochemical Effects:

Electrochemical effects were evident visually as a pH fluid wave during both modes of operation. The acid-base shift migrated based upon typical solution densities, but could be directionalized based upon configuration of the protective housing. The pH of the primary reaction zone demonstrated a range between 0.25 and 1.75 unit pH drop until energy delivery was terminated at which time rapid normalization occurred. This phenomenon was more evident during the gas production mode.

Collectable Gas Production:

Gas production was difficult to generate until higher levels of non-ablation energy delivery at which an increase in thermal gradients and acid-base fluid waves was evident. The collected gas was not condensable within the collection tube indicating the lack of water vapor production. Gas chromatography and mass spectrometry produced uniform species results in all instances with a 2:1 ratio of hydrogen and oxygen commingled gas without atmospheric contamination. Consistent with the constituent make-up of the collected gas, the gas bubble dynamics were different from that of water vapor bubble production used as a control. When compared to water vapor bubbles, the bubbles reached release state from the electrode very rapidly, were small in size on the order of a 125× smaller volume, remained spherical without confirmation fluctuations typical of the much larger water vapor bubbles, did not coalesce with other bubbles, demonstrated directional mass transfer fluid delivery properties, and displayed a slower terminal velocity. Gas bubble flow dynamics were easily modulated with the protective housing throttling vent/plenum.

Far-Field Characterization
Electromagnetic Field Characterization:

During operation, particles were not sensed by the radiation and particle detector above standard background which averaged approximately 2.5 mSv/yr at the testing locale. After 30 minutes of exposure to both non-ablation radiofrequency energy deposition and control a particle source, only the $\alpha$ particle source area was exposed. The area immediately adjacent to the electrode remained unexposed and clear of any image. Non-ablation radiofrequency energy produced only non-ionizing electromagnetic forces.

Treatment Site Characterization
Stoichiometry:

The observations of this study allowed formulation of a uniform stoichiometric thermochemical description of the near-field effects of non-ablation radiofrequency deposition upon interfacing media and are depicted in FIGS. 5 A-D. The overall process utilizes alternating current to rapidly spit and reconstitute water in a Repetitive Molecular Energy Conversion Loop. The general, electrothermal, electrochemical, and gas production observations are governed by the relative availability of the reactants and products within the primary reaction zone. The initial splitting of water is slightly endothermic driven by the low current and high activation overpotential of non-ablation radiofrequency energy. In this setting, gas emanation is very inefficient as bubble threshold fluencies and bubble lifetime dictate aqueous nano-sized bubble production that are immediately converted back to water. As gas emanation is produced, bubble size remained very small with high release rates; therefore, the electrode-to-fluid interface surface area was not significantly altered by gas production at any setting thereby limiting significant electrode current density or impedance fluctuations. This phenomenon was further supported by the high voltage potentials delivered which diminish any minimal effect of bubble induced conduction area reduction. As gas 220 emanation occurs and gas is liberated from the primary reaction zone by buoyancy forces, complementary liberation of additional acid-base pairs necessarily occurs that can be used for therapeutic interventions, both of which may be modulated by the protective housing throttling vent/plenum. The entire process is modifiable based upon a given relative salt concentration in solution that serves as a reaction salt-bridge catalyst influencing the Repetitive Molecular Energy Conversion Loop efficiency.

Figure 6:
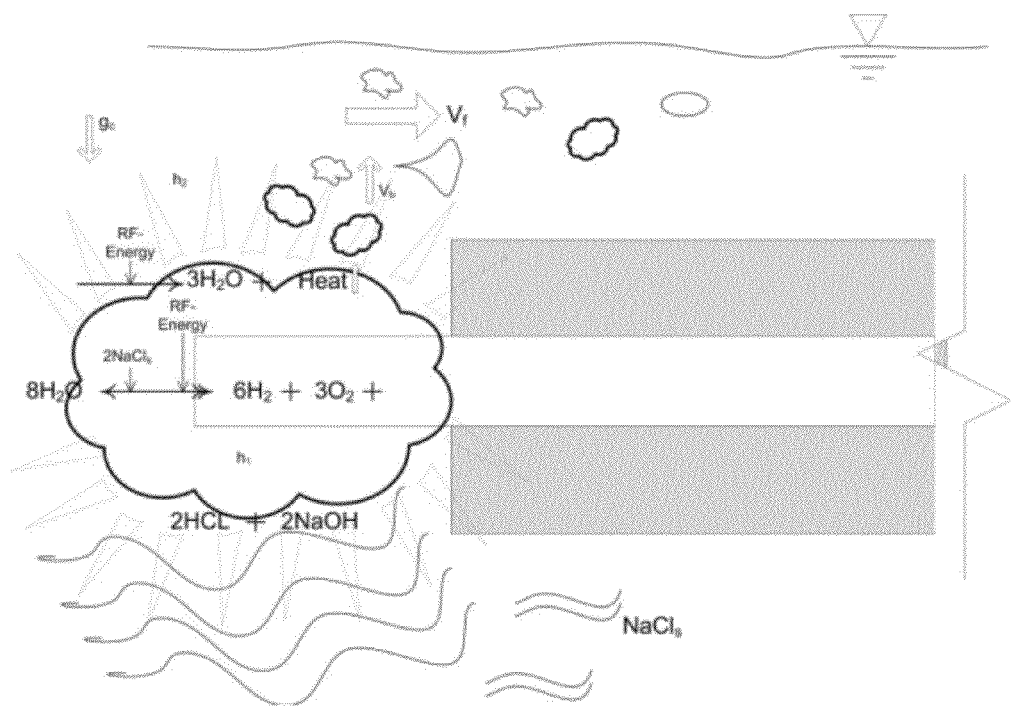
FIG. 6: Diagrammatic representation of the manipulation of saline interfacing media by non-ablative radiofrequency energy. Note that the protective housing is not shown for the purposes of illustration.

Representational Model:

FIG. 6 illustrates a representational model summarizing non-ablation radiofrequency energy manipulation of interfacing media with overlaid equations on the representation of the physical flow-field. The electrode provides conducted electrical energy to the electrode-fluid interface through the a salt ion solution whereby water splitting causes the accumulation of oxygen and hydrogen gases immediately about the electrode which rapidly reduce to water and heat. As the reaction takes place, buoyancy forces allow non-soluble gas to escape the primary reaction zone; while acid-base pairs of greater density descend away from the electrode with artifacts visible as density streak-lines. As the acid-base pairs move away from the electrode, cooling takes place which results in a normal precipitation. This reactant-product escape, although modulated by the protective housing, is facilitated by normal fluid flow in the surgical environment that, in addition, simultaneously induces considerable reaction zone quenching while preventing reaction zone water-starvation. Therefore, the Repetitive Molecular Energy Conversion Loop does not result in any volumetric loading of the primary reaction zone.

The results of this study demonstrate that non-ablation radiofrequency energy represents a new category of medical treatments that produce uniquely distinct near-field and far-field effects as electrical energy is converted to a therapeutically useful form. Near-field effects to perform surgical work are created by a thermochemical cycle originating directly from the molecular bond energy of water. This electrosurgical refinement creates an energy efficient procurement system that is a sister technology to other methods designed to capture released molecular energy from water like fuel cells, photolysis, and photosynthetic machinery. Non-ablation surgical devices utilize alternating current to rapidly split and reconstitute water in a Repetitive Molecular Energy Conversion Loop as a means to modify or precondition biologic tissues. Active electrode current density dispersion is manipulated by the protective housing to limit current delivery into tissues as current can be detrimental through tissue electrolysis and/or resistive (ohmic or Joule) heating. The near-field effects of current are delivered to the tissue surface rather than relying upon an electrode-to-tissue interface as in ablation-based devices designed to eliminate, coagulate, or dissect tissues. Because the near-field effects of current are geographically contained within the protective housing, these effects can be manipulated based upon procedure-specific needs with the protective housing serving as a mechanical adjunct to and selective throttling vent/plenum for energy and reactant-product delivery. The devices allow far-field electromagnetic forces to manifest within tissue unencumbered by current deposition and which are of intensities that do not create ionizing forces. A differential between current density dispersion and electromagnetic field strength is exploited to allow a normal healing response of tissues in response to the near-field treatment effects of tissue modification and preconditioning, while permitting far-field effects designed to induce therapeutic responses in the treated tissues that have been protected from the collateral damage of electrode-to-tissue interfaces.

The application of radiofrequency energy upon an electrically conductive media can follow distinct pathways based upon the nature of electrical work desired. These pathways are determined by structural rearrangements of water molecules that are subjected to the radiofrequency energy effects upon interfacing media molecular dynamics. Whether the interfacing media is in or around biologic tissues, it is governed by hydrogen bond behavior and proton transport that allow for widely malleable structural fluctuations of liquid water molecules. These fluctuations are due to water's very dynamic hydrogen bond network which displays the inherent ability to both exhibit simultaneous behavioral states and to rapidly reconfigure to accommodate physiochemical perturbations. With ablation- and plasma-based radiofrequency systems, resistive heating is produced predominantly by molecular kinetic and vibrational motions occurring within and amongst the hydrogen bond network. Rapid and intense resistive heating can produce a phase transition from liquid water to water vapor as vibrational motions further exert a predominate role in the ultrafast loss of liquid water's structural memory leading toward phase transition. This process is energy intensive due the high specific heat capacity and heat of vaporization of water. In the presence of charged species like salts, this temperature driven phase transition process from rapid resistive heating at the electrode is slowed by 3-4 times, which further increases the amount of energy required to reach phase transition. Once phase transition occurs, water vapor can be ionized by the electromagnetic forces associated with this radiofrequency energy level required to drive the heating process to phase transition. In contrast, non-ablation radiofrequency energy requirements are low because the energy input required is limited to splitting water which then creates a Repetitive Molecular Energy Conversion Loop that self-fuels due to the exothermic reaction of water reconstitution. Charged species like salts, in contrast to their effect during resistive heating, decrease the system energy requirements because they serve as a energy salt-bridge catalyst facilitating water splitting by forming, breaking, and nucleating hydrogen bonds between acid-base pairs and water molecules. As this study demonstrates, water splitting is a low energy initiation process associated with non-ionizing electromagnetic forces. It is for this reason that ablation-based systems have been designed with ever increasing energy levels and associated ionizing electromagnetic forces while non-ablation systems have focused upon limiting energy requirements by refining the energy procurement and delivery process to preserve tissue.

The near-field electrothermal effects of non-ablation radiofrequency energy are governed by the nature of electrical work performed upon the intermolecular hydrogen bonds of water-based interfacing media. Energy generation is created by a Repetitive Molecular Energy Conversion Loop rather than by high energy resistive heating of water. Splitting water is a mildly endothermic reaction that is driven by the low-energy near-field effects of non-ablation current; whereas, reconstitution back to water is exothermic providing assistive energy for further Repetitive Molecular Energy Conversion Loops ultimately deployed for surgical work. The alternating current allows each electrode to perform each redox half-reaction, but the effects can vary between electrodes because of architectural nuances. The initial reaction activation barrier is the four electron oxidation of water to oxygen during the anode phase of water splitting. This barrier is overcome by increased voltage potentials between the electrodes rather than by increased current so that architectural nuances of the electrodes are primarily due to the magnitude of voltage potential difference rather than current density disparities. At frequencies employed, this process is very inefficient at producing non-soluble gas. When non-soluble gas is produced, it is limited to molecular hydrogen and oxygen which is effectively managed by the protective housing throttling vent/plenum. Water vapor is not produced demonstrating the low-level energy deployment well below water's heat of vaporization. As a corollary, excessive water vapor production during resistive heating has been shown to significantly impair visualization of the ablation treatment site.

The near-field electrochemical events of non-ablation radiofrequency energy are also governed by the nature of electrical work performed upon the water-based interfacing media. During the Repetitive Molecular Energy Conversion Loop, alternating current can also facilitate an otherwise inefficient and more complex chemical reaction within the interfacing media rather than simple phase transition to water vapor as in ablation-based devices. The intermediary products and reactants of the Repetitive Molecular Energy Conversion Loop may combine to create an acid-base shift desirable for therapeutic interventions through techniques such as capacitive deionization and concentration enrichment. Because of the protective housing throttling vent/plenum, these products can be delivered in a controlled and localized fashion through precipitation, sedimentation, thermal, or chemical gradient forces into the treatment site through redox magnetohydrodynamic fluid flow. Much like the electrothermal gradients, these electrochemical modification gradients can be driven toward tissue surfaces.

For example, sodium hypochlorite can be precipitated preferentially based upon device design configuration to react with a wide variety of biomolecules including nucleic acids, fatty acid groups, cholesterol, and proteins at tissue surfaces. Additionally, pH shifts have been shown to produce tissue surface alterations effecting transport properties and extracellular composition. Water vapor itself is not a therapeutic product or event, limiting ablation-based devices to thermal interventions.

The far-field effects of non-ablation radiofrequency devices can manifest due to a minimal current density at or within biologic tissues, and hence magnetic field flux densities within the protective housing, and a high voltage potential force resulting in non-ionizing electromagnetic intensities designed for therapeutic use. Not only do these high voltage potentials increase the ability to perform redox reactions in conductive media by facilitating the Repetitive Molecular Energy Conversion Loop, voltage potentials not coincidentally have been shown to be a principle driver of non-ionizing electromagnetic effects upon biologic tissue. Because these electromagnetic forces carry energy that can be imparted to biologic tissue with which it interacts, higher voltage potentials enable oxidization or reduction of energetically more demanding tissue constituent macromolecular compounds other than water. These forces are deployed at the protective housing-to-tissue interface, unencumbered by current deposition, typically scaled at 0.5-1.5 mm distances from the electrode, rather than processes at the electrode-to-tissue interface as in, for example, plasma-based systems where the ionizing electromagnetic radiation generates high energy thermal particles that interact with biologic tissue.

Once non-ionizing electromagnetic fields have been produced from a given charge distribution, other charged objects within the field, such as biologic tissue, will experience a force, creating a dynamic entity that causes other tissue charges and currents to move as their strengths are typically lower. When non-ionizing electromagnetic radiation is incident on biologic tissue, it may produce mild thermal and/or weaker non-thermal field effects. The complex biological consequences of these fields, exerted through such mechanisms as tissue voltage sensor domains, stress response gene expression, and direct voltage-to-force energy conversion molecular motors, and their therapeutic potential for tissue healing are becoming more fully understood.

EXAMPLE 1

The Superficial Zone of articular cartilage has been implicated as a driver of chondrocyte migration and zonal reorganization in response to articular cartilage lesions and therefore may be a therapeutic target for healing induction. Previous studies have demonstrated chondrocyte proliferation, gene expression modification, temporal changes in matrix production, and lacuna formation in response to single exposure electromagnetic fields. The purpose of this example was to evaluate the effects of in situ targeted alternating current voltage potentials on native chondrocytes in vivo at the margins of full-thickness defects.

Full-thickness margin-stable femoral trochlea articular cartilage lesions exhibiting thick walls with smooth surfaces where identified during knee arthroscopy. Two groups were fashioned retrospectively based upon treatment: Group 1 received expectant treatment; Group 2 received a targeted constant alternating current voltage potential of 240V at 460 kH applied to the lesion margins without significant current deposition via a non-ablation medical device probe according to one embodiment of the present invention. Patients that underwent a second-look arthroscopy were included for study and the lesions were characterized. Patients with ligament injuries were excluded.

Figure 7:
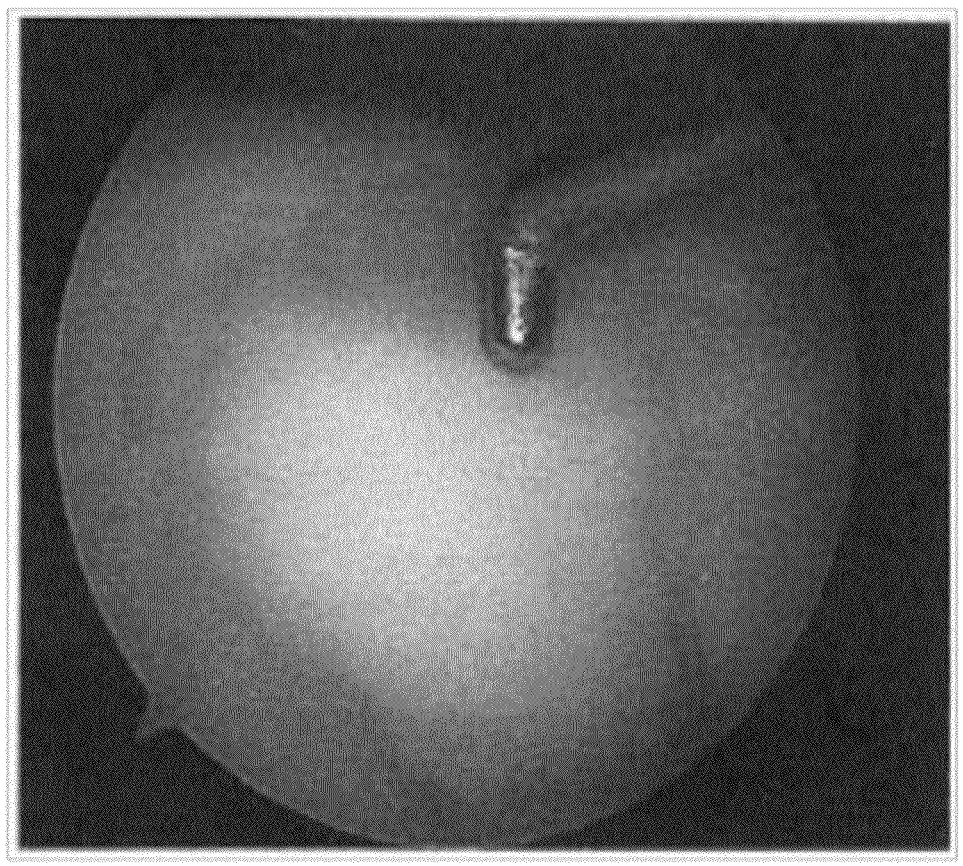
FIG. 7 illustrates a previous full thickness cartilage defect of the femoral trochlea which is now filled with cartilage-like tissue after treatment with high voltage potentials and a minimization of current deposition into the tissue at the treatment site.

The initial size of the femoral trochlea lesions was between 90-140 mm. Group 1 and 2 lesions exhibited little change in size, surface character, or margin stability at second-look. Group 2 lesions exhibited a filing-in of the defect with firm, cartilage-like tissue in 28% of patients at mean second-look follow up of 7.5 months (see FIG. 7).

This example provides additional evidence that alternating voltage potentials without current deposition delivered in situ can induce a chondrocyte response in native articular cartilage at the disease locale. Untreated margin-stable femoral trochlea lesions with thick walls and smooth surfaces did not progress during the follow up period; yet these lesions can be manipulated to display easily observable clinical behavioral changes. Superficial articular chondrocytes may be a good therapeutic target for non-destructive electromagnetic energy An embodiment of the present invention relates to an electrosurgical tool which has a plenum disposed at least partially around an active electrode, the plenum having one or more openings which permit fluid to enter the plenum chamber, and the plenum shielding tissue from the active electrode. The tool can also have a plurality of active electrodes and/or a plurality of openings in the plenum. An exterior surface of the plenum can be textured, which texture can be a roughened surface. Optionally, the plenum can have a shape useful for a surgical procedure, which can include a knife blade, which knife blade can optionally be serrated. In one embodiment, the openings can be on an end-portion of the plenum. The plenum can have at least one elongated opening orientated along its primary axis, or a plurality of elongated openings orientated along its primary axis. In one embodiment, the active electrode itself does not have any openings, flow-through channels, portals, and/or windows.

An embodiment of the present invention also relates to a method for performing an electrosurgical procedure which includes providing an electrosurgical apparatus having active and return electrodes; and disposing a plenum around the active electrode, the plenum comprising one or more openings which permit entry of fluid while preventing anatomically-specific tissue structures from contacting the active electrode. The anatomically-specific tissue can be targeted tissue and/or intact tissue. Optionally, the openings of the plenum can be disposed along a primary axis of the plenum. In the method, at least a portion of the plenum can extend beyond at least a tip of the active electrode. In one embodiment, the plenum does not comprise merely a recessed electrode.

An embodiment of the present invention relates to an electrosurgical tool having a plenum disposed at least partially around an active electrode, the plenum having a plurality of openings which permit fluid to enter the plenum chamber. The openings in the plenum can be small enough to inhibit and/or prevent the ability of intact tissue from entering the plenum. The openings in the plenum also act as a throttle or vent to allow redox magnetohydrodynamic fluid flow. The vent permits the redox magnetohydrodynamic fluid flow to be directed to the treatment site and/or prevents the wash out of the reactants by the fluid media as would occur if the tip of the active electrode were outside of the plenum.

An embodiment of the present invention also relates to an electrosurgical tool having a plenum disposed at least partially around an active electrode, the plenum having one or more openings which permit fluid to enter the plenum chamber, the openings being less than about 100% of any side of the plenum. Optionally, the openings can be less than about 80%, 70%, 50% or 35% of any side of the plenum.

An embodiment of the present invention also relates to an electrosurgical tool having a plenum disposed at least partially around an active electrode, the plenum having one or more openings which permit fluid to enter a chamber of the plenum, the plenum not entirely open on a tip thereof. The openings can be small enough to inhibit the ability of intact tissue from entering the plenum. The openings can be small enough to prevent intact tissue from entering the plenum.

An embodiment of the present invention also relates to an electrosurgical tool having an electrode surrounded on all sides by a plenum surface, the plenum surface having one or more openings which provide fluid flow and communication of a fluid past the active electrode. In one embodiment, the shape, size, and/or location of the one or more openings can be selected such that the fluid travels past the active electrode at a predetermined velocity.

In one embodiment, the present invention allows the general field of electrosurgery to use electrosurgical generators to power devices, such as instrument probes, developed for use in surgical and medical procedures.

As used throughout the specification and claims of this application, the term "plenum" is given a broad meaning and is intended to mean any type of a cage, guard, protective structure, or other device, system, method, apparatus, capable of at least partially housing an active electrode and inhibiting the ability for the active electrode to come into contact with a portion of tissue which is outside of the plenum. The term "plenum" also includes a device, method or apparatus that regulates the media and products by providing a mechanism for mechanically restricting the inflow of fluid and the outflow of the endogenously produced gases during electrosurgery at or about the active (working) electrode(s). The term "plenum" does not mean a mere slightly concave structure which permits tissue to come into contact with the active electrode when the tissue is pressed against the plenum.

Figure 9:
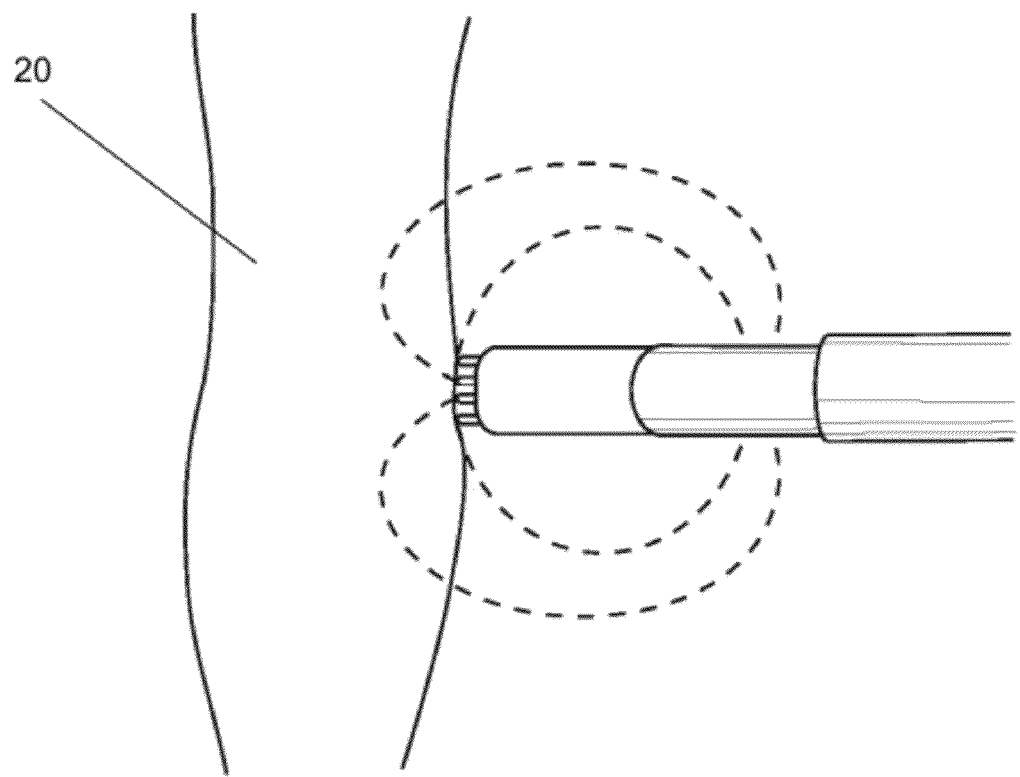
FIG. 9 is a drawing which respectively illustrates an prior art pressed against tissue and the theoretical current flow lines from the active electrodes to the return electrodes therefrom.

As illustrated in FIG. 9 (B) prior art electrosurgical devices 1 typically comprise one or more exposed active electrodes 2 which project from an end thereof. In typical electrosurgical applications, the surgical site is submerged in a conductive saline solution. The high frequency electric current flowing through the active electrodes and into the patient thus encounters differing amounts of impedance dependent upon whether the probe is contacting tissue of the patient or only the interfacing media. Accordingly, differing amounts of power are provided to the surgical site as the active electrodes 2 come in and out of contact with tissue of the patient.

Figure 8:
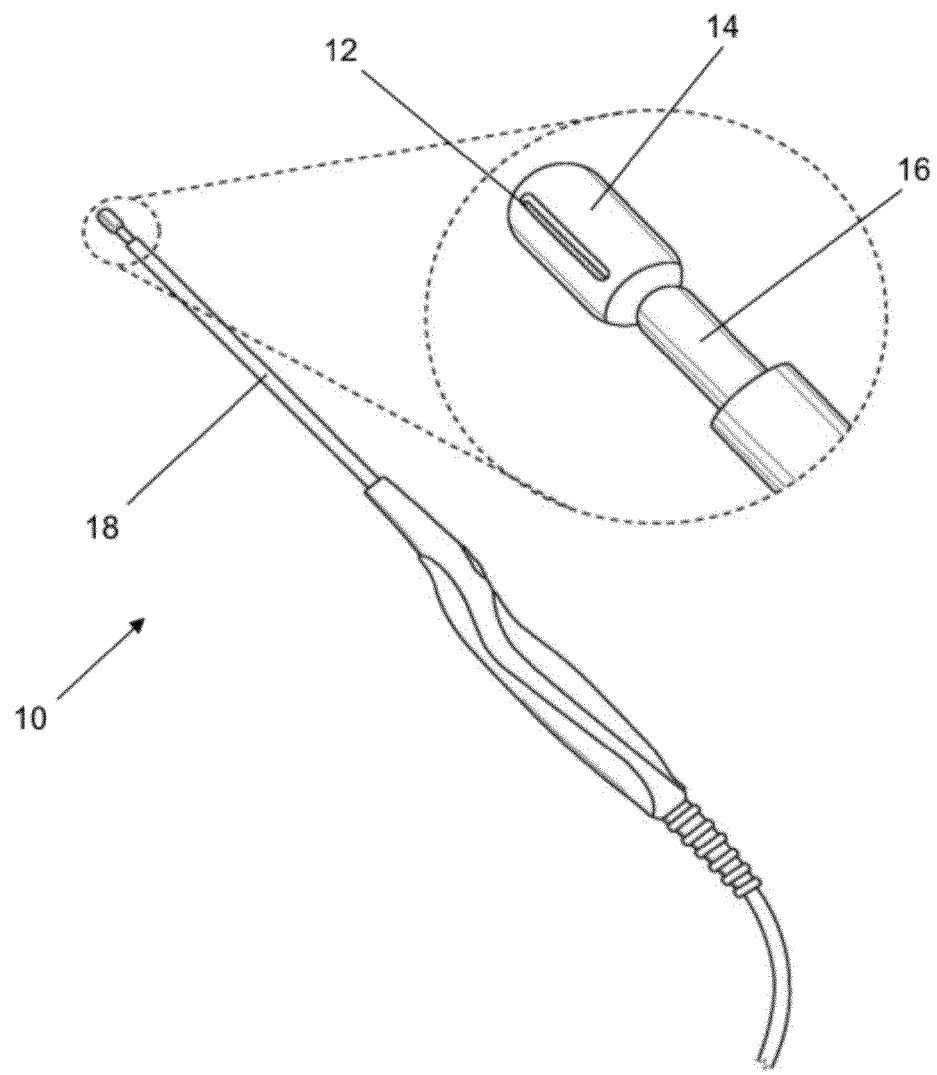
FIG. 8 illustrates an embodiment of the present invention whereby the electrosurgical device has a plenum disposed on its tip which prevents the active electrode from contacting adherent living tissue during an electrosurgical procedure and allows all the elements of electrosurgery to inter mingle or be brought to the active (working) electrode.

As illustrated in FIG. 8, one embodiment of the present invention comprises electrosurgical probe 10 having active electrode 12 housed within insulating plenum 14. Desirable results can be obtained when probe 10 is operated in a monopolar mode or a bipolar mode. When operated in a bi-polar mode, return electrode 16 is optionally disposed slightly proximal along lumen 18 from insulating plenum 14. In an alternative embodiment, an active and reference electrodes can optionally be disposed within insulating plenum 14. In yet another embodiment active electrode 12 can be housed within plenum 14 and plenum 14 can optionally be formed from a conductive material and used as a return electrode or as a portion of the return electrode.

In a preferred embodiment, insulating plenum 14 is made from a non-conductive material which most preferably comprises a glass, ceramic, or other material which can withstand high electric voltage and high temperatures whereby the plenum is a mechanical implement used to assist or for treatment.

Figure 10:
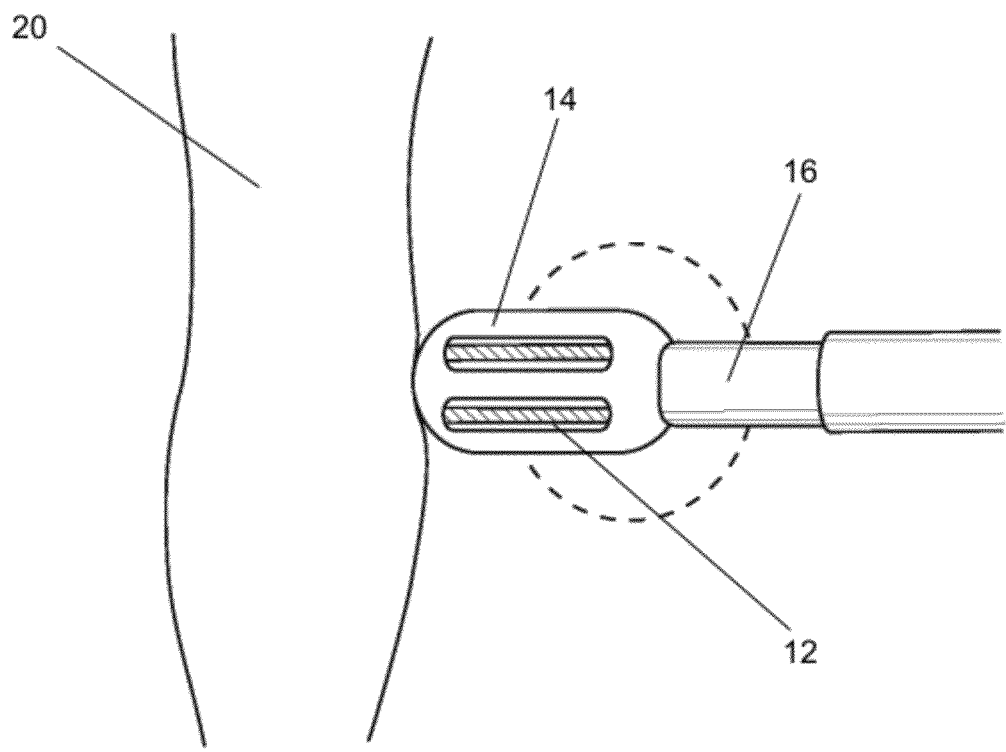
FIG. 10 is a drawing which respectively illustrates an embodiment of a present invention device pressed against tissue and the theoretical current flow lines from the active electrodes to the return electrodes therefrom.

As illustrated in FIGS. 9 and 10, which respectively illustrate the prior art probe and the probe of the present invention each contacting tissue 20 at a surgical site. The dashed lines illustrate current flow paths from the active electrodes to the return electrode. As can be seen in the drawings, the current flow paths, and thus impedance, is much more constant and predictable with the probe of the present invention since only the fluid at the surgical site acts as the conductor between the active and return electrodes, whereas the tissue also acts to conduct the flow of electricity with the prior art device, particularly when the active electrode is in contact therewith. Not only does the present invention thus permit a more constant and predictable amount of power to be delivered to a surgical site, and thus more predictable surgical results, but the present invention also greatly reduces the potential for significant current flow through the tissue, such current flow can cause damage to the tissue, thus making the present invention a safer surgical tool than the devices of the prior art. Furthermore, the shape of the electrode can then be optimized for its electrical properties rather than for tissue interfacing properties which all prior art exemplifies. For example, a sharpened edge of the active (working) electrode provides for beneficial electrical properties in a conductive or electrolyzable environment by optimizing current density at the solid (electrode)/fluid (interfacing media) contact points as opposed to within the tissue as all prior art exemplifies.

In one embodiment, the opening in the plenum is preferably dimensioned for specific procedures to protect tissue of the most common anatomical dimension expected to be encountered in the specific procedure from entering the plenum.

Embodiments of the present invention preferably provide the reduction and/or elimination of excessive field-effect transistor, OP-Amp, and/or inductor usage in the construction of primary radio frequency ("RF") delivery circuitry within electrosurgical console unit ("ESU"). The outcome of voltage standing wave ratio stabilization is less heat production within the ESU and the reduction in size of the ESU. Where probe designs hold total impedance to 100Ω or less, console sizes can preferably be reduced by as much as 50%-75% in size. This provides a mechanism by which ESU's can be designed to fit ever-increasing limits in space and space competition within the operating room for consoles specific to various procedures. Further, as the size decreases, it may be housed within the hand piece of the device itself make the electrosurgical probe cordless, with a self-contained power source and circuitry.

More specifically, in one embodiment, the present invention relates to specific methods of connection of such devices to electrosurgical generators that provide active enhancement of output signal monitoring. Embodiments of the present invention also relate to specific management of circuit characterization when a single mode output from an electrosurgical generator is bridged to perform a circuit contraction in physical space. Embodiments of the present invention also preferably provide improved system level reliability as there is a significant reduction in the system's dependency upon software for maximum output power governance and emergency shut-down. In some embodiments, the present invention can be used in real-time electrophoresis or drug-infusion (patch) technology (battery powered drug patches that accelerate drug infusion).

Fluid Flow. The plenum controls the fluid flow and hence the treatment site reactions. It also allows for the fluid flow to buffer and/or protect the tissue in a cooling manner to avoid the application of excessive heat to the treatment site. The fluid or media can be configured more specifically, like fluids, gels, semi solids and the like that are either conductive or electrolyzable. The plenum also protects the primary reaction zone from the surgical environment at the treatment site which can be unpredictable with the encompassing fluid flow such as during arthroscopy.

Electrical. Since the present invention provides the ability for the active/working electrode to operate without touching the tissue, impedance changes far less than in other prior art devices because the tissue, which is the prime driver of impedance change during treatment, is not involved. Impedance fluctuations are buffered so as to better control energy deposition at the treatment site. The present invention also, allows different configurations of the power source, and makes the stability of power deposition at the treatment site safer. Sensing devices are also able to be more effectively used since impedance is no longer necessarily the prime measurement that is used for feedback control. This permits numerous sensors to optionally be used, including but not limited to temperature sensors and pH sensors as more fully described in U.S. patent application Ser. No. 11/006,079. Electrode architecture is developed based upon voltage potential disparities rather than current density disparities.

The general form of the function for impedance of the arthroscopic electrosurgical circuit in-vivo can be approximated by the following generalized function:

$$Z_{TOT} = f[(z_{tissue} + z_{media} + z_{probe}), x, t]$$

If the objective is to understand time-variation of this function it follows that:

$$\frac{\partial Z_{TOT}}{\partial t} = \frac{\partial z_{tissue}}{\partial t} + \frac{\partial z_{media}}{\partial t} + \frac{\partial z_{probe}}{\partial t} + \frac{\partial x}{\partial t} + 0$$

However, in traditional contact electrosurgery, the limits of distance of probe to target tissue site are known to approach zero (i.e. the electrode must contact the tissue):

$$\lim_{x \to 0} \frac{\partial Z_{TOT}}{\partial t} = \frac{\partial z_{tissue}}{\partial t} = \frac{\partial z_{media}}{\partial t} + \frac{\partial z_{probe}}{\partial t} + 0;$$

Additionally, it is important to note that the internal probe impedance with respect to time is effectively a constant:

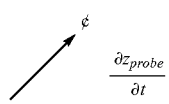

This is because the conductors within the probe consist of stable elements of copper wire conductors whose metallic conductance values (material resistivities) vary little, and therefore do not significantly contribute to the time based variation of impedance.

What remains as the dominant elements of impedance time-based variation is:

$$\lim_{x \to 0} \frac{\partial Z_{TOT}}{\partial t} = \frac{\partial z_{tissue}}{\partial t} + \frac{\partial z_{media}}{\partial t} + \phi \quad \text{(Eq.-1)}$$

Of these elements, the known values for media conductivity (NaCl, 0.09% by weight) are relatively constant even given a relatively small amount of thermal variation in bulk fluid properties (Resistivity typically in the range of 80-110 Ω-cm). This can be restated as: 95 Ω-cm±15 Ω-cm; illustrating that the relative magnitude of impedance shift (variance) within the media alone represents approximately a 16% variation.

Next, reviewing known parameters of tissue induced impedance in the electrosurgical circuit when in direct contact with probe active electrodes; many electrosurgical manuals indicate that load impedances typically exceed 500Ω into a variety of tissue types. Even under the assumption of equivalent variation (16% of nominal, 500Ω) the total impedance change is equal to 79Ω. This represents a five-fold (5×) increase in overall impedance from that of the interfacing media alone. If we use this nominal approach we can rewrite Eq.-1, above as:

$$\lim_{x \to 0} \frac{\partial Z_{TOT}}{\partial t} = 5\left[\frac{\partial z_{media}}{\partial}\right] + \frac{\partial z_{media}}{\partial} + \phi; \quad \text{(Eq.-2)}$$

What this reveals is that during application of RF energy to tissue in domains below plasma, tissue impedance is the dominant factor by at least half an order of magnitude. It is worthy of note, that typical impedance variations have been noted in the laboratory that exceed 30% in tissue contacting electrosurgery which amplifies the stark magnitude difference in Eq.-2 to an even larger extent.

It should now be straightforward to understand that RF electrosurgery, when controlled below plasma levels, provides a more stable impedance environment and enables a more predictable output response of probe technology in relation to applied power. When the benefits of protected electrodes are introduced in below plasma controlled RF electrosurgery Eq.-2 is now dominated only by media impedance variations and is rewritten as follows:

$$\lim_{x \to 0} \frac{\partial Z_{TOT}}{\partial t} = \frac{\partial z_{media}}{\partial} + \phi$$

But this was already identified as being 95 Ω-cm±15 Ω-cm, previously. Thus, RF signal/power generator feedback fluctuations for protected electrodes no longer have to deal with rapid and significant swings in Voltage Standing Wave Ratios (VSWRs) and the need for rapid response software control of current flow and voltage output is minimized. FIGS. 1 and 2, below illustrate the differences practically between the Prior-Art and the new State-of-the-Art introduced by NSI.

Embodiments of the present invention provide a protected electrode geometry combined with the reductions in dynamic impedance change that is inherently part of a protected electrode architecture. These embodiments thus provide a more stable platform of low-energy RF electrosurgery below plasma domains. As such, clinicians can benefit from the many and varied applications of RF energy on various tissue types that provide for more complete healing response and lower energy deposition to target tissue sites. These provide the benefit of less harm to healthy tissue and a more complete participation of surrounding tissue, which unharmed by virtue of this architecture, in the overall healing response.

Embodiments of the present invention provide a reduction or elimination of the mismatched impedance of a load in an electrosurgical circuit created by variations that are naturally occurring when tissue contacting electrodes are utilized. Traditional electrosurgery has involved the direct contact of active electrode elements with human tissue where the end result has been to cut, dissect, or ablate the tissue structure. Since the characteristic impedance of such tissue structures is primarily defined by their relative water/electrolyte content (NaCl) as the typical procedure progresses with an electrode in direct contact with tissue, there is a desiccating function that naturally reduces this electrolyte content and thus raises the characteristic impedance during sustained application of RF energy to a target tissue site. This process also induces metabolic effects that the host tissue needs to accommodate.

Typically electrical feedback circuitry built into electrosurgical units (ESUs) are designed to detect high-impedance reflections causing Voltage Standing Wave Ratio's (VSWR) within the primary RF output circuit, defined as:

$$VSWR = \frac{(1+\Gamma)}{1-\Gamma}, \text{ where: } \Gamma = \frac{(z_L - z_o)}{(z_L + z_o)},$$

Note that the source impedance $Z_o$, is essentially that defined by the ESU, connector, cable and the Probe. The Load impedance $Z_L$, is the impedance of the interfacing media, tissue, and return electrode. What becomes evident to those skilled in the art, is the time-varying nature of the impedance and its functionally dependant variables. The raw interfacing media, most commonly NaCl (0.5%-0.9% by weight) has a nominal impedance of 55Ω-100Ω depending on a host of variables that include:

a. Tissue type being contacted (water/electrolyte content)
b. Temperature of the interfacing media
c. Distance of the active electrode to tissue structures
d. Bulk velocity of the fluid field immediately about the active electrode
e. Exposed surface area of the active electrode
f. Distance between the active and return electrodes
g. Random field effects of physio-chemical actions including electrolysis Embodiments of the present invention provide protected electrode probe configurations thus eliminating the variations caused by (a) and drastically limit those caused by (b) above. As contact with tissue is by design prevented, the total impedance variations with time are drastically reduced that could result from tissue desiccation. Current pathways are provided for in the electrode design that can traverse adjacent to tissue from the active electrode to the return electrode through the interfacing media only without affectation by the tissue or its relative conductivity as determined by its state of hydration. This technique as disclosed herein allows for a more specific involvement of the interfacing fluid/media by which the energy of the electrosurgical generator is transferred or deposited at the treatment site. The work of this energy is on the interfacing media primarily, and avoids the higher current densities within tissue of the prior art. These interfacing media interaction are those that would occur within a conductive or electrolyzable media.

When one considers the remaining variables it is clear that (b) and (d) are strongly related as the bulk velocity increases, the temperature will approach the constant of the bulk bag temperature of the saline fluid being infused. Note also that (e) and (f) are fixed quantities based on the specific design of the probe under evaluation. Also note that the protected electrode design limits the minimum distance that the active electrode can be brought toward tissue. The net result is that of the variables at play, in a protected electrode probe design, only (g) remains as a major player in control variables.

For energy levels in the COAG domain (0-180 Watts output power), (g) is nearly linear and increases with output power. This stabilization of large variations in impedance through elimination and reduction of component impedance functions within the electrosurgical environment result in lower VSWR's in the transmission lines of the ESU and Probe. When such conditions are minimized an output circuit is said to be "matched" to its impedance load. While these conditions will not be exact due to the technique dependent factors at play intra-operatively, they are significantly reduced, creating a safer device.

In one embodiment, a preferable distance is from about 0.5 mm to about 5 mm. More preferably, distances of active electrode protection range from about 0.5 mm to about 2 mm.

An embodiment of the present invention relates to an electronic bridging circuit which includes one or more circuit components arranged in electrical communication with a primary radiofrequency active or reference/return electrode lead of a hand piece of an electrosurgical generator upon which lead a super-imposed rider wave signal is transmitted, the super-imposed wave signal normalized to a monopolar balanced state of feedback to the electrosurgical generator reference plate electrode monitoring circuit via the one or more circuit components; the one or more circuit components selected to affect the super-imposed wave signal by balancing the rider signal; and wherein monopolar outputs of the electrosurgical generator are converted to bipolar outputs compatible with the hand piece upon connection of hand piece with the generator. In the circuit, a plurality of the circuit components can be connected in a parallel configuration, a series configuration, or a combination thereof. The circuit components can include a capacitor, an inductor, a resistor or pluralities and/or combinations thereof. If a capacitor is provided, it can optionally have a value of about 1 picofarad to a value of about 1 microfarad, more preferably about 40 picofarads to a value of about 0.1 microfarad. Optionally, one or more of the components can be arranged in a bridge circuit.

An embodiment of the present invention also relates to an electrosurgical apparatus comprising a conventionally-shaped monopolar output universal plug for the delivery of primary RF electrical current, which comprises no more than two of the typical three conductors.

An embodiment of the present invention also relates to a method for converting a monopolar electrosurgical generator which outputs a power wave and a super-imposed rider wave for use in a bipolar electrosurgical configuration which method includes bridging leads connected to the monopolar electrosurgical generator with a bridging circuit having at least one balancing component, the balancing component selected such that the impedance encountered by the rider wave when traveling through a bipolar hand piece and the balancing component is substantially similar to the impedance encountered by the rider wave when a monopolar hand piece and return pad is connected to the electrosurgical generator. The balancing component can be disposed within the bipolar hand piece. The balancing component can comprise a plurality of components which can be active, resistive, or a combination thereof. The bipolar hand piece can be electrically connected to only one of the cut or coagulate outputs of the monopolar electrosurgical generator.

An embodiment of the present invention also relates to a method for using a monopolar output of an electrosurgical generator for a bipolar electrosurgical application which method includes connecting a plurality of active electrodes of a bipolar electrosurgical hand piece to an active electrode port of a monopolar electrosurgical generator; providing one or more components through which a reference signal passes, the one or more components selected such that the total impedance encountered by the reference signal is at least substantially similar to a total impedance which would be encountered by the reference signal if it were traveling through a functioning monopolar electrosurgical hand piece. At least one of the plurality of active electrodes can be connected to the active electrode port of the monopolar electrosurgical generator through a switch. Optionally, each of a plurality of the active electrodes can be connected to the active electrode port of the monopolar electrosurgical generator through respective switches. The plurality of active electrodes can be individually and/or simultaneously activated.

An embodiment of the present invention relates to an electrosurgical apparatus which includes a monopolar electrosurgical generator connected to a bipolar electrosurgical hand piece. The hand piece can operate in a cut only mode or in a coagulate only mode.

An embodiment of the present invention also relates to a bipolar electrosurgical hand piece connectable and operable with a monopolar electrosurgical generator.

In an alternative embodiment, the electrosurgical hand piece of each of the foregoing embodiments can be operable in-situ and optionally with a liquid environment about a tip of the hand piece.

It should become obvious to those skilled in the art that use of those same materials from which conductive wiring elements are constructed namely, the individual wiring conductors, can be adapted to create a portion or all of the necessary impedance effect for use in the bridge circuit. This can most easily accomplished through use of wiring configurations such as coaxial, twisted pair, interlaced pairing, or helix winding of conductors that influences the overall nominal capacitance of any given length of cable section used to conduct both the primary RF electrical power and simultaneously the return/reference electrical signal.

Additionally, it should also become obvious to those skilled in the art, that mere length changes, whether alone or in combination with conductor configurations cited above can be used to effectively tune cable assemblies to desired impedance levels alone or in combination with those active/passive circuit additions to a bridging circuit as disclosed herein.

Results

Six patients yielding six separate specimens originating from femoral condyle resection were included for study. All devices performed as suggested by manufacturer in their respective Instructions for Use (IFU) and publications on their respective performance. Each of the devices successfully completed a chondroplasty procedure as determined by the executing surgeon and later confirmed by a panel of three peer surgeons.

From the six specimens, twenty-four osteochondral samples were tested (n=6 per Group; total sample parts=24). Three sections of each specimen were prepared and mounted on slides for scanning via a confocal microscope.

The clearest and most appropriately focused of the three sections from each sample were scanned and photographed. The photographed sections had the live and dead cells counted on a "per mm2" basis to determine live and dead cell density. Then the deepest dead cell from each section was identified and a measurement was made between that cell and the nearest section of cartilage surface.

Control Specimens Histology

The control specimens demonstrate typical fibrillated articular surfaces consistent with gross visual inspection of the harvested tissues and an Outerbridge Grade III classification. The Superficial Zone was clearly disrupted by the fibrillation, but chondrocytes with a flattened chondron appearance typical of this zone remained present even toward the base of the fibrillation. In all control specimens, the fibrillation did not penetrate to the Transitional Zone of the cartilage tissue. Within the fibrillated tissue itself, live cells were observed residing within the tissue at varying distances from the surface of the fibrillation. Live cells were abundantly present in density patterns typical of healthy cartilage around and below the surface fibrillation. Cell population densities within each specimen group remained constant as the samples of each group originated from the same specimen. Inter-specimen comparisons did not reveal significant differences in relative cell population densities, chondron orientation, or cellular distribution patterns confirming similar lesion type included for study. Occasional dead cells were observed to reside in a more extruded position within the fibrillation itself but not within the substance of the morphologically intact cartilage tissue. Adjacent to the fibrillated segments, a more typical Outerbridge Grade II appearance was observed without fibrillation but with loss of surface cellularity and lacunar emptying within the Superficial Zone below the lamina splendens.

Ablation Device 1 Treated Specimens

In the ablation device 1 treated samples, large charred tissue segments and loss of cartilage thickness above that of control were observed throughout the treatment site. Tissue charring ranged from light-brownish color to near black or dark grey indicating severe char and tissue damage. There were areas of tissue fragmentation indicating ablation extraction of tissue as is typically observed during standard electrocautery procedures. No treated specimens yielded either a visually or histologically smooth cartilage surface even though the initial fibrillation of the specimens was eliminated. The fibrillated tissue surface was replaced with a residual layer of necrotic and damaged tissue in all instances. No specimen exhibited Superficial Zone characteristics due to the tissue loss that had occurred. Cellular density and chondrocyte characteristics of the residual tissue under the necrotic layer was markedly decreased and consistent with control specimen Transitional Zone cartilage depth, indicating significant loss of tissue exceeding the level of disease pre-treatment. Dead cells were present under the charred surfaces in all specimens and occasionally intermixed with live cells. Due to the normally decreased cellular density of the Transitional Zone, the residual tissue under the charred layer exhibited dead cells in a widely distributed pattern within the cartilage matrix indicating significant penetration of the treatment through the extracellular matrix tissue and into deep chondrons.

Ablation Device 2 Treated Specimens

In the ablation device 2 treated samples, generalized gelatinization of tissue was observed at the treatment site indicative of altered matrix properties. The gelatinized tissue was observed to have a semi-translucent appearance and much softer consistency than the surrounding cartilage. Slightly less bulk loss of normal cartilage was observed when compared to the ablation device 1 specimens. In some areas, however, tissue charring in the same geometric pattern as that of the active electrode was visually noticeable in the treatment area. This observation was termed ablation electrode imprinting and was distinctly noticeable due to the unique ring shape of the ablation device 2 electrode. A firmer consistency of the cartilage adjacent to the ablation electrode imprinting was noted with a more typical ablation tissue extraction pattern observed at the site of imprinting. All specimens yielded a surface elimination of the original fibrillated cartilage tissue and a resultant layer of post-treatment necrotic tissue; and, all with some areas of ablation tissue extraction similar to the ablation device 1 samples and the goal of tissue ablation. The residual tissue exhibited some latent Superficial Zone characteristics such as elongated chondrons parallel to the articular surface. Abundant dead cells were intermixed with some live cells throughout the entire Superficial Zone in all specimens with additional dead cells observed into the superficial part of the Transitional Zone.

Non-Ablation Device According to One Embodiment of the Present Invention Treated Specimens In the following example a non-ablative device according to one embodiment of the present invention treats samples the fibrillated cartilage tissue was removed resulting in a smooth residual surface at the treatment site. No areas of charred, gelatinized, or color altered tissue were observed at the treatment site consistent with the non-ablative type of energy delivered. All specimens yielded a residual tissue bed demonstrating similar appearance and consistency to that of the non-fibrillated tissue surrounding the treatment site. All specimens retained intact Superficial Zone characteristics in the residual tissue below the level of removed fibrillation without areas of necrosis or dead cells. Accordingly, no specimen part demonstrated additional bulk tissue loss other than that of the diseased fibrillated cartilage. Live cells were evident throughout the residual treatment site with chondrocytes residing closer to the surface than that noted in the non-fibrillated sections of the control specimens of each sample. This finding indicated an increased surface-based level of cellularity post-treatment in the retained Superficial Zone of the treatment site.

Quantitative Analysis of Cell Viability and Depth of Necrosis

Four data sets were analyzed quantitatively. Live and dead cells were counted within a similarly located and sized area of scanned specimen. The results were reported as # of live cells per mm2 and # of dead cells per mm2. Additionally, the deepest dead cell was located and a depth measurement was made between that cell and the surface of the cartilage section. As the qualitative review of the histology showed, non-ablation device according to one embodiment of the present invention successfully relieves the tissue of dead cells while preserving live cells in a higher density than the original diseased tissue. Ablation device 2 treatment resulted in the death of ⅓ of the cells, while ablation device 1 resulted in the death of almost ⅔ of the cells.

Dead Cell Density vs. Duration of RF Delivery

Figure 12:
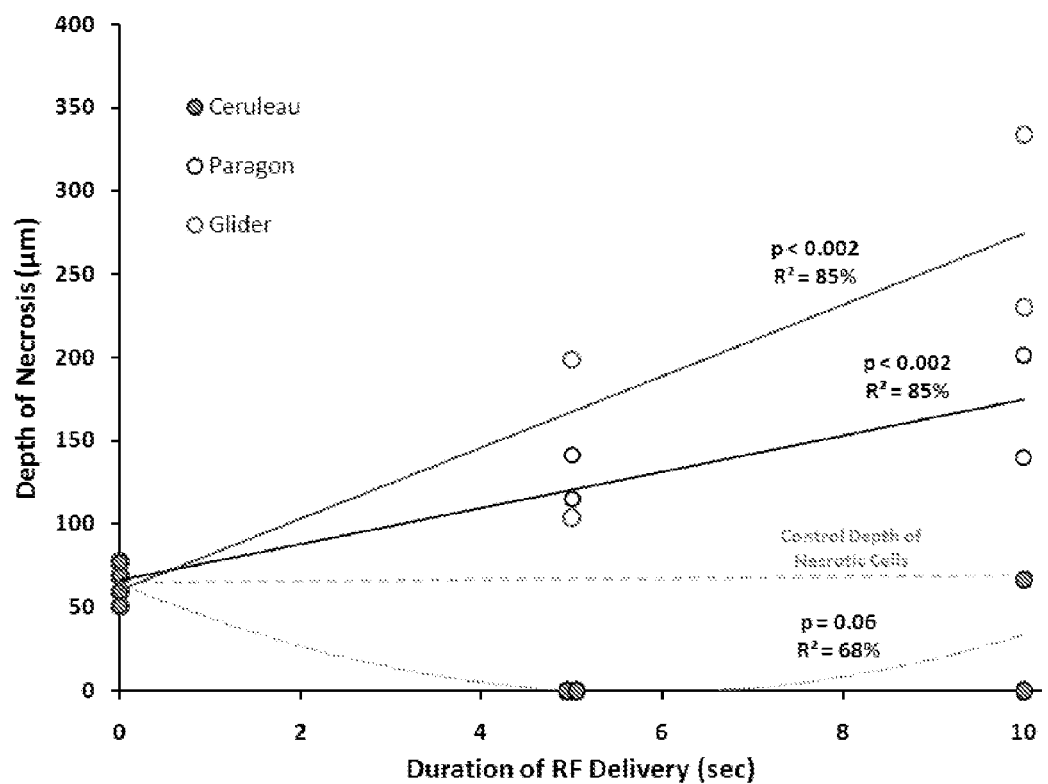
FIG. 12: Graph showing the average depth of necrosis seen with each of the devices. Depth of necrosis advances in a linear fashion for both the ablation device 2 and the ablation device 1. There was no cell death for non-ablation device according to one embodiment of the present invention at 5 seconds (n=2) and only 1 of the 2 samples at 10 seconds showed cell death that was on par with the starting depth of necrosis.

Two time periods were examined with a 5 and 10 second application of RF as evenly distributed over the lesion sample as possible. The progression of cell death is examined in FIG. 12 as the treatment is applied for 5 vs. 10 seconds. The curve fits for progression for all of the following sections are in Appendix H. The ablation device 1 results and the subsequent curve fit imply a very rapid rise in dead cell density. The ablation device 1 design has an electrode that is flush with the tissue and insulator surface but fully incorporated within the insulator. This design eliminates any chance of convective cooling from the super-fusing fluid while the electrode is emitting RF. This means that the RF subsurface resistive heating creates a heat pool that is undamped by cooling while the tip is in place. The longer this delivery phenomenon exists, the more the heat will spread down the thermal gradient, killing all cells that reach a critical temperature (approximately 48° C.).

The ablation device 2 delivers energy in the same manner, but the curve is different because the electrode design allows some convective cooling from the superfusate that acts as a damper to the thermal spread, thus the slight lag in the rise in % dead cells concentration. The thermal pool still develops but it is slightly buffered by the presence of a contra-acting cooling vent. Once established, however, the thermal momentum doesn't exhibit slowing. For non-ablation device according to one embodiment of the present invention, two sections at 5 seconds and one of the sections at 10 seconds showed no dead cells. The single sample showing cell death counted 66 cells/mm2 and the dead cells were well distributed throughout the sample, not concentrated as with the ablation device 2 and ablation device 1. Although a curve could be fit to non-ablation device according to one embodiment of the present invention results, based on a $Y=A-\sqrt{(BX)}$ equation, it is purely used to illustrate the overall trend since the equation has yet to demonstrate physical relevancy.

As in the paragraph titled Dead Cell Density vs. Duration of RF Delivery, the average depth of necrosis measures were analyzed in respect to application time. Linear relationships were seen between the deepest points of necrosis and application duration for both ablation device 1 and ablation device 2. As before, the ablation device 1 necrosis is much more rapid than ablation device 2. In this analysis, non-ablation device according to one embodiment of the present invention results didn't fit a curve to a statistically significant level. A parabolic (polynomial regression to the 2nd power) does reveal a nice trending. As with the % cell death slide, the curve fit doesn't necessarily represent a physically viable mechanism and is therefore only included as an aesthetic visual aid. It should be noted that even at 10 seconds when necrotic cells are found in a non-ablation device according to one embodiment of the present invention treated sample, the # of dead cells is less than that in the control, 3% vs. 10%, while the depth of necrosis remains equal to the average value of the depth of necrosis for the control samples (66 μm vs. 64±12 μm).

During this protocol the non-ablation device according to one embodiment of the present invention and the two ablation devices were used to treat samples of excised diseased human cartilage with grade II and III chondromalacia. Non-ablation device according to one embodiment of the present invention outperformed the competitive devices qualitatively, quantitatively and retrospectively. It has long been thought that successful chondroplasty must come at the expense of collateral damage. Non-ablation device according to one embodiment of the present invention uses traditional RF energy from common boxes in a manner very similar to other devices with the noted exception of the prevention of active electrode contact with the tissue surface. This feature, along with the use of a protective insulator allows for any thermal mechanisms of action to be generated within a confined space of the protective insulator not within the targeted tissue. The additional feature of using a COAG Valleylab wave form that is significantly biased towards voltage rather than current appears to prevent the generation of intra-tissue sub-surface electrically generated heat pools.

Figure 11:
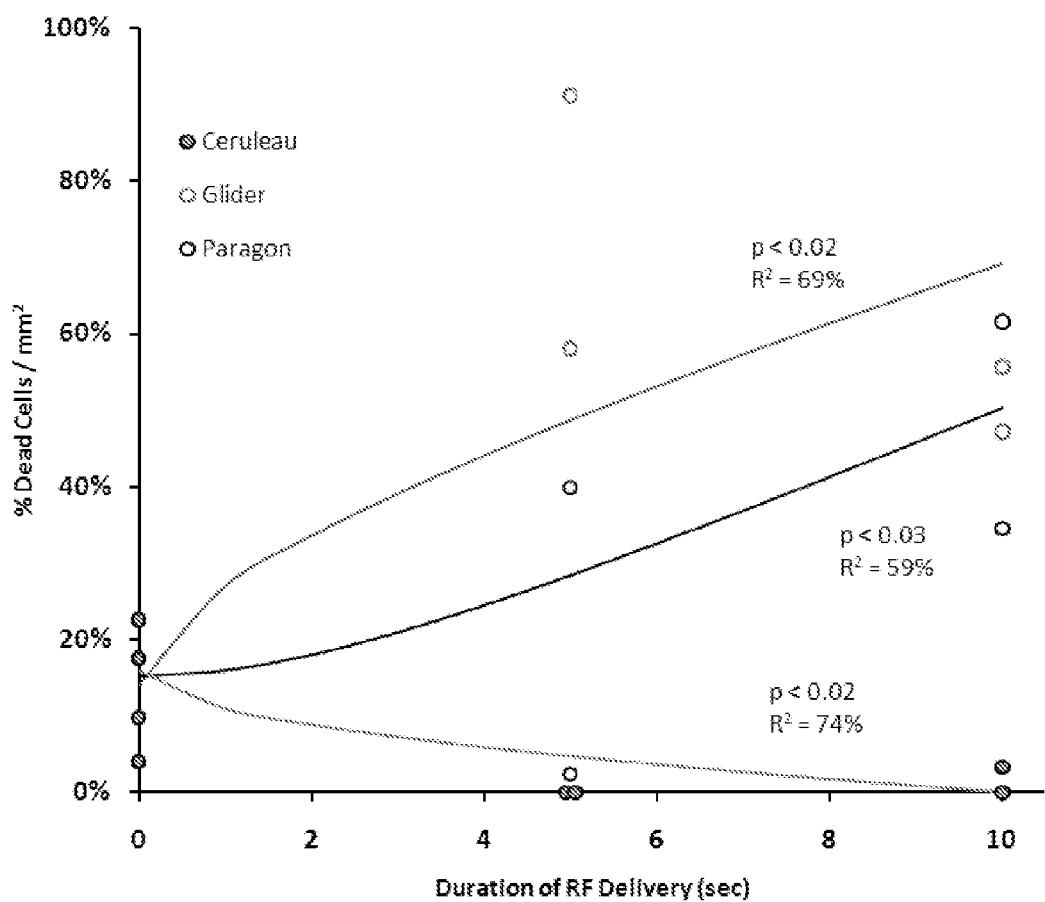
FIG. 11: This figure demonstrates the progression of cell death during the RF exposure time for all three probes tested for the purposes of illustration. The control values were used for the starting (time 0) point of all of the probes. Ablation device 1 ($p<0.02$) and ablation device 2 ($p<0.03$) each had statistically significant curve fits albeit with moderate correlation (ablation device 1 $R2$ 69%, cc=0.83; ablation device 2 $R2$ 59%, cc=0.77). Non-ablation device according to one embodiment of the present invention histology showed no cell death in both 5 second application and one 10 second. The curve fit (although statistically significant) isn't appropriately based in physics, but it does show an opposite mechanism to the conventional ablation-based device approaches of prior art.

The complete lack of cell death in 75% of the non-ablation device according to one embodiment of the present invention samples is striking, and there is a 100% trend of a reversal in both the number and extent of dead cells compared to traditional RF designs. The curves fit from % cell death in FIG. 11 show that ablation device 2 does succeed in reducing the thermal injury more than ablation device 1 by damping the subsurface thermal pool via the open active tip design allowing convection via superfusing media. If only thermodynamic mechanisms are in play, then the non-ablation device according to one embodiment of the present invention results (curve) indicate that its design either takes much better advantage of the available cooling, or it amplifies the effects in some way. Amplification isn't physically possible without an active cooling mechanism within the probe. Therefore the only thermodynamic explanation would be that non-ablation device according to one embodiment of the present invention takes better advantage of the convective cooling of the media. Published literature has shown that the superficial layer of articular cartilage is resistive to fluid movement, a key feature giving articular cartilage its mechanical impact buffering capability. If a thermal pool is created within the tissue, the capability for convective thermal transfer would be severely restricted and a reliance on thermal conduction to the surface through the surface layer would greatly limit the efficacy of the convective process. Ablation device 1 compounds the issue by delivering RF deep into tissue and eliminating convection by insulating the whole region surrounding the active electrode from fluid flow. Ablation device 2 allows some remnant convection through the open design of the looped electrode, but the proximity of the active electrode to tissue still delivers current deep into the tissue creating the subsurface thermal pool. Non-ablation device according to one embodiment of the present invention's thermal pool is created within its protective insulator. This results in two advantages. First, any thermal effects on cartilage are working their way into the tissue via conduction, this process will be in full exposure to the convection of media. This allows, the second advantage, when energy is terminated, the lingering effects are negligible since convective cooling occurs at a much higher rate than thermal conduction. In contrast, a thermal pool created within cartilage can remain for many seconds after termination of energy delivery, a large enough one could therefore keep killing cells well after a conventionally designed RF device (having a tissue contacting electrode) is turned off.

Although the invention has been described in detail with particular reference to preferred embodiments and examples, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

Although the description above contains many specific examples, these should not be construed as limiting the scope of the invention but merely providing illustrations of some of the presently preferred embodiments of this invention. Thus, the scope of the invention should be determined by the appended claims and their legal equivalents, rather than narrowed by the specific illustrative examples given.

The invention claimed is:

1. A method for inducing a therapeutic response in living tissue while minimizing current deposition in living tissue, the method comprising:

providing a probe to an aqueous salt ion solution of a treatment site where a therapeutic response in living tissue is desired wherein the probe includes an active electrode and a return electrode separated by an insulator and wherein the living tissue is separated from the active electrode by a plenum housing the active electrode;

immersing of at least the portion of the probe and plenum including the active electrode and the return electrode in the aqueous salt ion solution;

positioning the plenum housing the active electrode in close proximity to the treatment site, the active electrode and return electrode being immersed in the aqueous salt ion solution; and applying a high voltage potential between the electrodes to deliver an electromagnetic non-ionizing radiation to the living tissue at the treatment site to induce a therapeutic response in the living tissue.

2. The method of claim 1 wherein the therapeutic response is activation of tissue voltage sensor domains, stress response gene expression, direct voltage-to-force energy conversion molecular motors, and cell proliferation.

3. The method of claim 1 wherein the high voltage potential between the active electrode and return electrode does not create temperatures to cause water vapor as the current applied to generate the high voltage potential is below that to cause water vapor when acting in an aqueous environment.

4. The method of claim 1 wherein applying a high voltage potential between the electrodes in the aqueous salt ion solution generates a redox magnetohydrodynamic fluid flow that recharges reactants near the active electrode located within the plenum and wherein the plenum vents the fluid flow to the treatment site.

5. The method of claim 1 further comprising treating tissue at the treatment site with reactants from a redox magnetohydrodynamic fluid flow reaction as a result of creating a high voltage potential between the active and return electrodes.

6. The method of claim 1 wherein the plenum protects a primary reaction zone from convective forces at the treatment site.

7. A method of performing an electrosurgical procedure on a patient to produce a therapeutic response, the method comprising:

providing a surgical probe including an active electrode and a return electrode separated by an insulator wherein the active electrode is located within a plenum of the probe;

providing an aqueous salt ion environment at the location wherein the electrosurgical procedure is to be performed, the environment comprising sufficient volume to permit immersion of at least the portion of the surgical probe including the active electrode within the plenum and the return electrode;

positioning the electrodes and plenum so as to immerse the probe in the aqueous salt ion environment; and applying current to a circuit comprising the active electrode and return electrode, the current being less than that required to induce plasma ionization, but sufficient to induce a repetitive molecular energy conversion loop from a portion of the aqueous salt ion environment to produce a therapeutic response at the treatment site.

8. The method of claim 7 wherein the therapeutic response is a healing response.

9. The method of claim 8 wherein the healing response comprises one or more of the following: activation of tissue voltage sensor domains, stress response gene expression, direct voltage-to-force energy conversion molecular motors activation, or cell proliferation.

10. The method of claim 7 further comprising concentrating and or enriching the reactants or products of the repetitive molecular energy conversion loop in an aqueous environment for therapeutic use at a treatment site with the plenum.

11. The method of claim 7 wherein the plenum protects a primary reaction zone from convective forces of the treatment site.

* * * * *